(12) United States Patent
Hyodo et al.

(10) Patent No.: US 9,775,677 B2
(45) Date of Patent: Oct. 3, 2017

(54) MEDICAL TREATMENT TOOL AND MANIPULATOR INCLUDING THE SAME

(71) Applicant: OLYMPUS CORPORATION, Tokyo (JP)

(72) Inventors: Ryoji Hyodo, Tokyo (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 668 days.

(21) Appl. No.: 14/275,964

(22) Filed: May 13, 2014

(65) Prior Publication Data
US 2014/0249545 A1  Sep. 4, 2014

Related U.S. Application Data

(63) Continuation of application No. PCT/JP2012/080407, filed on Nov. 16, 2012.

(30) Foreign Application Priority Data

Nov. 16, 2011 (JP) .................................. 2011-250682

(51) Int. Cl.
*A61B 34/30* (2016.01)
*A61B 19/00* (2006.01)
*A61B 34/00* (2016.01)
*A61B 17/29* (2006.01)

(52) U.S. Cl.
CPC .......... *A61B 19/2203* (2013.01); *A61B 34/30* (2016.02); *A61B 34/71* (2016.02);
(Continued)

(58) Field of Classification Search
CPC ..... A61B 19/2203; A61B 34/30; A61B 34/71; A61B 2017/2919; A61B 2017/2922;
(Continued)

(56) References Cited

U.S. PATENT DOCUMENTS 4,038,987 A * 8/1977 Komiya ............... A61B 17/122
606/142
2002/0082617 A1 6/2002 Nishtala et al.
(Continued)

FOREIGN PATENT DOCUMENTS

DE    2506471 A1    8/1975
EP    1 872 729 A1  1/2008
(Continued)

OTHER PUBLICATIONS

Chinese Office Action dated Oct. 9, 2015 from related Chinese Patent Application No. 201280055686.3, together with an English language translation.
(Continued)

*Primary Examiner* — Gary Jackson
*Assistant Examiner* — Zahed Kabir
(74) *Attorney, Agent, or Firm* — Scully, Scott, Murphy & Presser, P.C.

(57) ABSTRACT

Provided is a medical treatment tool, the distance between a first advance and retraction axis, and a tip end is shorter than the length of the first link member, and the length when a line segment connecting the base end and the center of a forceps rotation shaft is projected on the first advance and retraction axis is shorter than the length is projected on the first advance and retraction axis. The distance between a second advance and retraction axis, and a tip end is shorter than the length of the second link member, and the length when a line segment connecting the base end and the center of a forceps rotation shaft is projected on the second advance and retraction axis is shorter than the length projected on the second advance and retraction axis.

8 Claims, 14 Drawing Sheets

(52) U.S. Cl.
CPC ............... *A61B 2017/2919* (2013.01); *A61B 2017/2922* (2013.01); *A61B 2017/2923* (2013.01); *A61B 2017/2938* (2013.01)

(58) Field of Classification Search
CPC .... A61B 2017/2923; A61B 2017/2983; A61B 17/29; A61B 2017/2926; A61B 2017/2927; A61B 2017/2929; A61B 2017/2932; A61B 2017/2938; A61B 2017/2939; A61B 18/1445; A61B 2034/742
USPC ............... 606/1; 128/123.1, 108; 81/306, 3
See application file for complete search history.

(56) References Cited

U.S. PATENT DOCUMENTS

| | | | |
|---|---|---|---|
| 2003/0135204 A1 | 7/2003 | Lee et al. | |
| 2005/0043758 A1* | 2/2005 | Golden | A61B 10/06 606/206 |
| 2008/0035701 A1* | 2/2008 | Racenet | A61B 17/07207 227/176.1 |
| 2008/0051631 A1 | 2/2008 | Dejima et al. | |
| 2009/0112230 A1* | 4/2009 | Jinno | B25J 9/104 606/130 |
| 2013/0331826 A1* | 12/2013 | Steege | A61B 17/2909 606/1 |

FOREIGN PATENT DOCUMENTS

| | | |
|---|---|---|
| JP | 6-1696 Y2 | 1/1994 |
| JP | 2007-301692 A | 11/2007 |
| JP | 2011-083476 A | 4/2011 |
| JP | 2012-187311 A | 10/2012 |

OTHER PUBLICATIONS

Extended Supplementary European Search Report dated Jul. 24, 2015 from related European Application 12 84 9810.2.
International Search Report dated Dec. 25, 2012 issued in PCT/JP2012/080407.

* cited by examiner

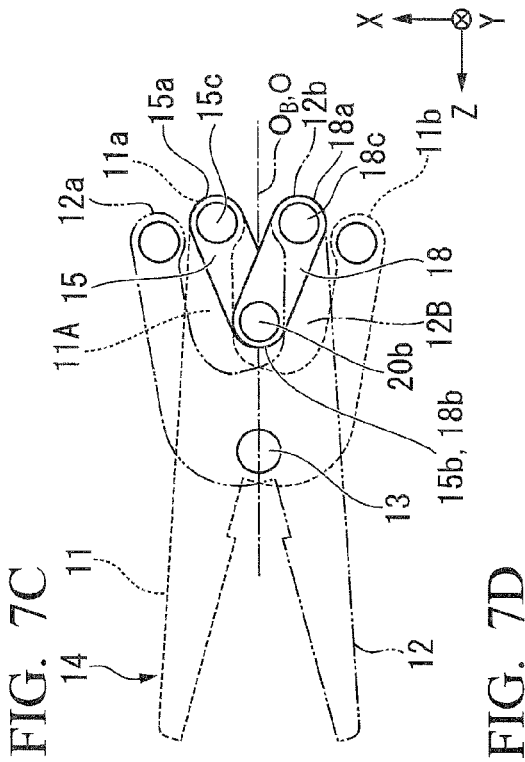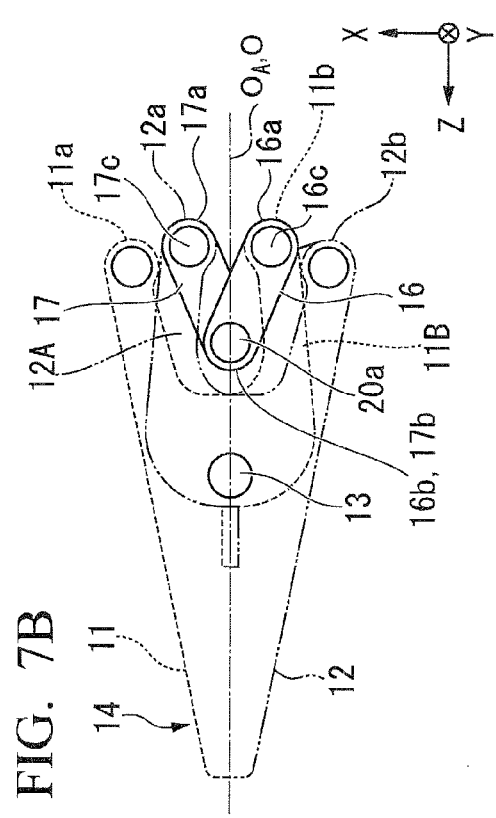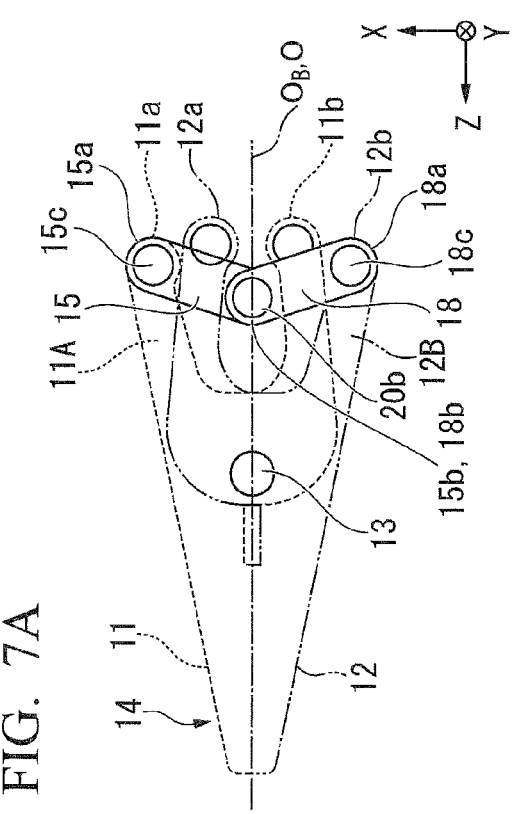
FIG. 7A  FIG. 7B  FIG. 7C  FIG. 7D

MEDICAL TREATMENT TOOL AND MANIPULATOR INCLUDING THE SAME

This application is a continuation application based on PCT/JP2012/080407, filed on Nov. 16, 2012, claiming priority based on Japanese Patent Application No. 2011-250682, filed Nov. 16, 2011. The contents of both the Japanese Patent Application and the PCT Application are incorporated herein by reference.

FIELD OF THE INVENTION

The present invention relates to a medical treatment tool and a manipulator including the same.

DESCRIPTION OF RELATED ART

In the related art, medical treatment tools that grasp or press living body tissues, surgical instruments, or the like for performing procedures are used in the medical field. These medical treatment tools are introduced into body cavities of a patient, and are used for various kinds of procedures by being attached to a manipulator that constitutes, for example, a master slave type medical manipulator system or being inserted through a forceps channel of an endoscope.

Japanese Examined Utility Model Application, Second Publication No. H06-1696 describes grasping forceps, as one of the medical treatment tools, including an openable and closable grasping part. A wire is connected to the grasping part via link mechanisms and the wire is inserted through a coiled sheath. If the wire is pushed and pulled and advanced and retracted in the longitudinal direction, the grasping part is opened and closed.

In the above grasping forceps, there are needs for further strengthening the grasping force of the grasping part so that tools, such as suture needles, tissues, or the like can be firmly grasped. In order to respond to this, Japanese Unexamined Patent Application, First Publication No. 2007-301692 suggests a manipulator including a so-called toggle mechanism (a booster mechanism or an energizing mechanism).

SUMMARY OF THE INVENTION

The medical treatment tool of a first aspect of the present invention is a medical treatment tool including a treatment section which has a pair of treatment tool pieces having a first treatment tool piece and a second treatment tool piece, at least one of the first treatment tool piece and the second treatment tool piece being rotatably supported with respect to a substrate; a first manipulating member which is provided so as to be movable along a advance and retraction direction with respect to the substrate and transmits a manipulation force caused by towing of rotating the pair of treatment tool pieces in a direction in which the pair of treatment tool pieces is opened; a second manipulating member which is provided so as to be movable along a direction parallel to the advance and retraction direction with respect to the substrate and transmits a manipulation force caused by towing of rotating the pair of treatment tool pieces in a direction in which the pair of treatment tool pieces is closed; a first link member which has a first end coupled to the pair of treatment tool pieces and a second end coupled to the first manipulating member; and a second link member which has a first end coupled to the pair of treatment tool pieces and a second end coupled to the second manipulating member. In the first link member, a distance between a first advance and retraction axis along which the second end advances and retracts with a movement of the first manipulating member, and the first end is shorter than a length of the first link member, and a length when a line segment connecting the second end and the rotation center of the pair of treatment tool pieces is projected on the first advance and retraction axis is shorter than a length when a line segment connecting the first end and the rotation center is projected on the first advance and retraction axis. In the second link member, a distance between a second advance and retraction axis along which the second end advances and retracts with a movement of the second manipulating member, and the first end is shorter than a length of the second link member, and a length when a line segment connecting the second end and the rotation center of the pair of treatment tool pieces is projected on the second advance and retraction axis is shorter than a length when a line segment connecting the first end and the rotation center is projected on the second advance and retraction axis.

In a medical treatment tool of a second aspect of the present invention, in the first aspect, the first treatment tool piece and the second treatment tool piece may be rotatably supported with respect to the substrate, the first treatment tool piece may be coupled with the first manipulating member via the first link member, and the second treatment tool piece may be coupled with the second manipulating member via the second link member.

In a medical treatment tool of a third aspect of the present invention, in the second aspect, the first link member coupled to the first treatment tool piece and the first link member coupled to the second treatment tool piece may be coupled to the first manipulating member via one first connection rotation shaft at the respective second ends thereof, and the second link member coupled to the first treatment tool piece and the second link member coupled to the second treatment tool piece may be coupled to the second manipulating member via one second connection rotation shaft at the respective second ends thereof.

In a medical treatment tool of a fourth aspect of the present invention, in the second aspect or the third aspect, the substrate may include a first guide that extends along the first advance and retraction axis and a second guide that extends along the second advance and retraction axis, the first manipulating member may be supported so as to be movable along the first guide, and the second manipulating member may be supported so as to be movable along the second guide.

In a medical treatment tool of a fifth aspect of the present invention, in any aspect of the first aspect to the fourth aspect, the medical treatment tool may further include a wire which has the first manipulating member and the second manipulating member coupled to one end and the other end thereof and a wire driving part which allows the first manipulating member to advance and retract along the first advance and retraction axis and allows the second manipulating member to advance and retract along the second advance and retraction axis by rotating and winding the wire.

In a medical treatment tool of a sixth aspect of the present invention, in any aspect of the first aspect to the fourth aspect, the medical treatment tool may further include a rack-and-pinion driving part that has a first rack, a second rack, and a pinion engaged with the first rack and the second rack, and that drives to advance and retract the first rack and the second rack in mutually opposite directions by a rotation of the pinion; a first wire that couples the first rack and the first manipulating member; and a second wire that couples the second rack and the second manipulating member. The wire is driven to advance and retract by the rack-and-pinion driving part to advance and retract the first manipulating member along the first advance and retraction axis and advance and retract the second manipulating member along the second advance and retraction axis.

In a medical treatment tool of a seventh aspect of the present invention, in the fifth aspect or the sixth aspect, a tension application portion that applies tension to the wire may be provided in a middle of the wire.

A manipulator of the present invention may include the medical treatment tool according to any one aspect of the first aspect to the seventh aspect.

BRIEF DESCRIPTION OF THE DRAWINGS

FIG. 7A is a schematic view showing the positional relationship between link members when the treatment section of the medical treatment tool of the first embodiment of the present invention is closed.

FIG. 7B is a schematic view showing the positional relationship between the link members when the treatment section of the medical treatment tool of the first embodiment of the present invention is closed.

FIG. 7C is a schematic view showing the positional relationship between the link members when the treatment section of the medical treatment tool of the first embodiment of the present invention is opened.

FIG. 7D is a schematic view showing the positional relationship between the link members when the treatment section of the medical treatment tool of the first embodiment of the present invention is opened.

DETAILED DESCRIPTION OF THE INVENTION

Figure 1:
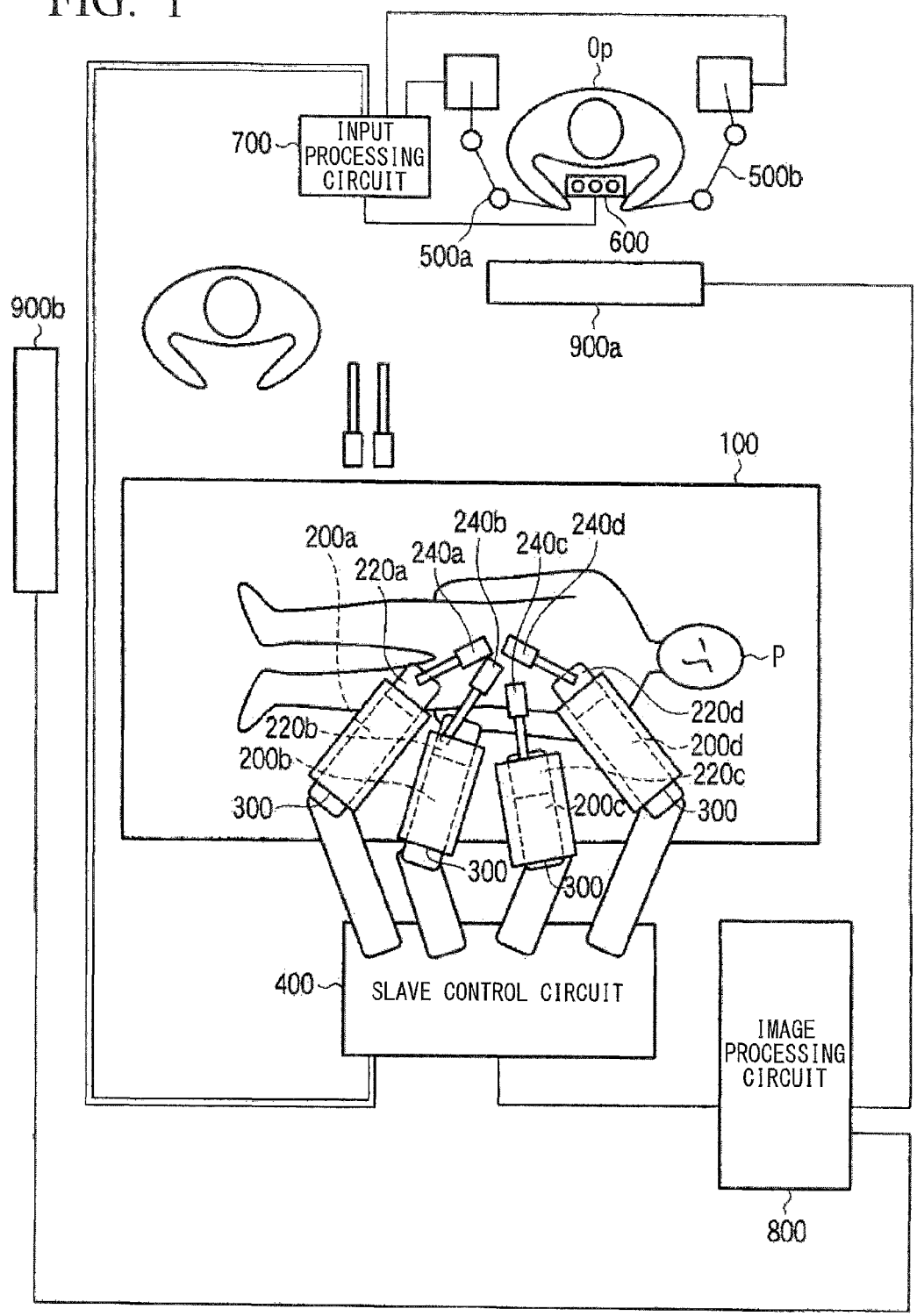
FIG. 1 is a schematic view showing an example of the configuration of a medical manipulator system to which a medical treatment tool of the present invention is applied.

Embodiments of the present invention will be described below with reference to the accompanying drawings. In all the drawings, even if embodiments are different, the same reference numerals will be given to the same or equivalent members, and common description will be omitted.

[First Embodiment]

Although a first embodiment of the present invention will be described below, an example of a medical treatment tool (hereinafter simply referred to as "treatment tool") of the present embodiment and a medical manipulator system to which the manipulator is applied will be described.

FIG. 1 is a schematic view showing an example of the configuration of a medical manipulator system to which a medical treatment tool of the present invention is applied.

An example of a master slave type medical manipulator system is shown in FIG. 1. The master slave type medical manipulator system is a system that has two kinds of arms including a master arm and a slave arm and remotely controls the slave arm so as to follow the operation of the master arm. The manipulator of the present invention can be applied as this slave arm.

The medical manipulator system shown in FIG. 1 has a surgical table 100, slave arms 200a, 200b, 200c, and 200d (manipulators), a slave control circuit 400, master arms 500a and 500b, a manipulating unit 600, an input processing circuit 700, an image processing circuit 800, a display 900a for an operator, and a display 900b for an assistant.

Hereinafter, in order to simplify description, symbols "Xa, Xb, . . . , Xz" in an alphabetical order may be expressed as "Xa to Xz". For example, the "slave arms 200a, 200b, 200c, and 200d" may be expressed as "slave arms 200a to 200d".

The surgical table 100 is a table on which a patient P who is a target to be observed and treated lies down. The plurality of slave arms 200a to 200d is installed in the vicinity of the surgical table 100. The slave arms 200a to 200d may be installed on the surgical table 100.

The slave arms 200a to 200d have a plurality of multi-degree-of-freedom joints, respectively, and bend the respective multi-degree-of-freedom joints, thereby positioning a treatment tool to be mounted on the tip ends (the side that faces the body cavity of the patient P) of the slave arms 200a to 200d with respect to the patient P lying on the surgical table 100. The respective multi-degree-of-freedom joints are individually driven by power units (not shown). As the power units, for example, motors (servo motors) having a servo mechanism including an incremental encoder, a decelerator, or the like can be used, and the motion control of the power unit is performed by the slave control circuit 400.

The slave arms 200a to 200d have a plurality of power units for driving mounted treatment tools 240a to 240d (not shown). As the power units, for example, servo motors can also be used, and the motion control of the power units is also performed by the slave control circuit 400.

In a case where the power units of the slave arms 200a to 200d are driven, the driving amounts of the power units are detected by position detectors. Detection signals from the position detectors are input to the slave control circuit 400, and the driving amounts of the slave arms 200a to 200d are detected in the slave control circuit 400 by the detection signals.

Power transmission adapters 220a, 220b, 220c, and 220d for operation (hereinafter simply referred to as "adapters") are interposed between the slave arms 200a to 200d and the treatment tools 240a to 240d to connect the slave arms 200a to 200d and the treatment tools 240a to 240d, respectively. The adapters 220a to 220d have driving mechanisms that drive the treatment tools 240a to 240d, respectively, and are configured so as to transmit the power generated in the power units of the corresponding slave arms to the corresponding treatment tools.

As the driving mechanisms of the adapters 220a to 220d, linear-motion mechanisms, rotating mechanisms, or the like are provided according to the configuration of corresponding treatment tools.

The slave control circuit 400 is configured to have, for example, a CPU, a memory, or the like. The slave control circuit 400 stores a predetermined program for performing the control of the slave arms 200a to 200d, and controls the operation of the slave arms 200a to 200d or the treatment tools 240a to 240d according to a control signal from the input processing circuit 700. That is, the slave control circuit 400 specifies a slave arm (or treatment tool) that is a manipulation target of a master arm manipulated by the operator Op on the basis of the control signal from the input processing circuit 700, and computes a driving amount that is required to cause the specified slave arm to make a movement corresponding to the degree of movement of the master arm by the operator Op.

Also, the slave control circuit 400 controls the operation of a slave arm or the like that is a manipulation target of the master arm according to the computed driving amount. In this case, the slave control circuit 400 inputs a driving signal to a corresponding slave arm, and controls the magnitude or polarity of the driving signal so that the driving amount of the slave arm that is a manipulation target becomes a target driving amount according to a detection signal input from a position detector of a power unit according to the operation of the corresponding slave arm.

The master arms 500a and 500b are constituted by a plurality of link mechanisms. Respective links that constitute the link mechanisms are provided with, for example, position detectors, such as an incremental encoder. By detecting the operation of the respective links using the position detectors, the degree of movements of the master arms 500a and 500b are detected in the input processing circuit 700.

The medical manipulator system of FIG. 1 needs to manipulate four slave arms using two master arms 500a and 500b and appropriately switch the slave arms that are manipulation targets of the master arms. Such switching is performed, for example, by the manipulation of the manipulating unit 600 by the operator Op. Of course, such a change is unnecessary if manipulation targets have a 1-to-1 correspondence by making the number of master arms and the number of slave arms the same.

The manipulating unit 600 has switching buttons for switching the slave arms that are manipulation targets of the master arms 500a and 500b, and various kinds of manipulating members, such as a scaling changing switch that changes the operation ratio of a slave and a master, and a foot switch for urgently stopping the system. In a case where a certain manipulating member that constitutes the manipulating unit 600 is manipulated by the operator Op, a manipulation signal according to the manipulation of the corresponding manipulating member is input to the input processing circuit 700 from the manipulating unit 600.

The input processing circuit 700 analyzes the manipulation signals from the master arms 500a and 500b and the manipulation signal from the manipulating unit 600, and generates a control signal for controlling the medical manipulator system according to an analysis result of the manipulation signal, to input the control signal to the slave control circuit 400.

The image processing circuit 800 performs various kinds of image processing for displaying an image signal input from the slave control circuit 400, to generate image data for display in the display 900a for an operator and the display 900b for an assistant. The display 900a for an operator and the display 900b for an assistant are constituted by, for example, liquid crystal displays, and displays an image based on the image data generated in the image processing circuit 800 according to an image signal acquired via the observation instrument.

In the medical manipulator system configured as described above, if the operator Op manipulates the master arms 500a and 500b, a corresponding slave arm and a treatment tool attached to this slave arm operate in response to the movement of the master arms 500a and 500b. Thereby, a desired procedure can be performed on Patient P.

Next, the medical treatment tool of the present embodiment will be described.

Figure 2A:
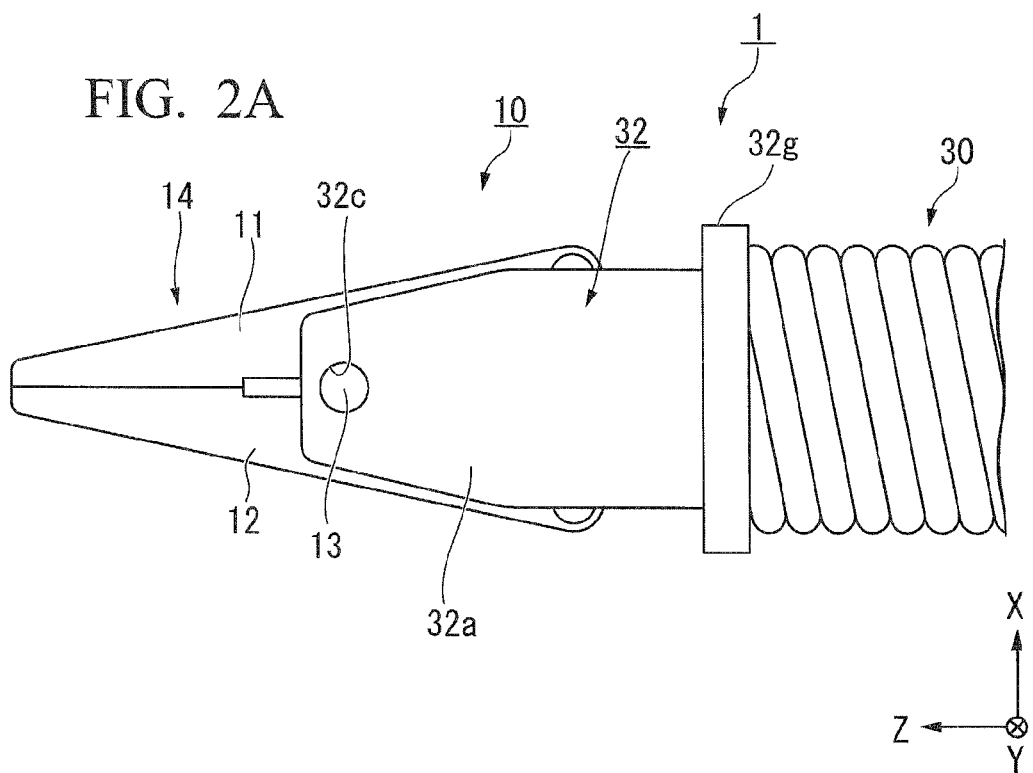
FIG. 2A is a schematic front view showing a tip end of a medical treatment tool of a first embodiment of the present invention.
Figure 2B:
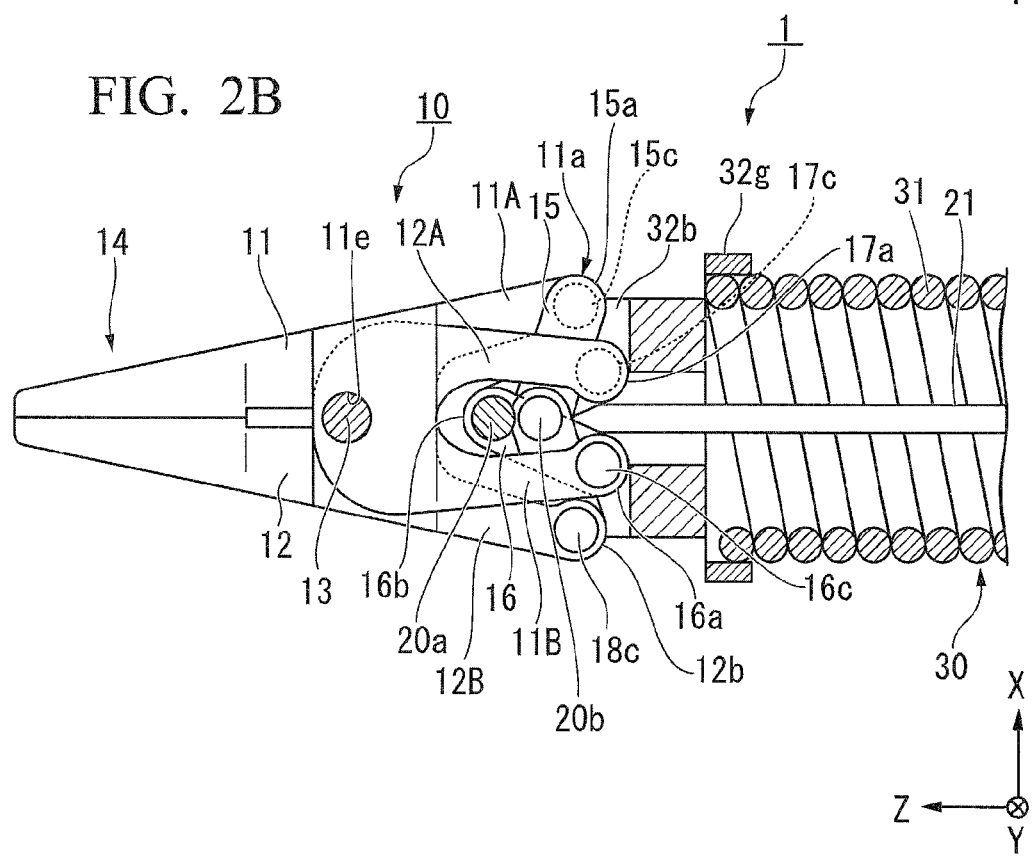
FIG. 2B is a schematic cross-sectional view showing the tip end of the medical treatment tool of the first embodiment of the present invention.
Figure 3:
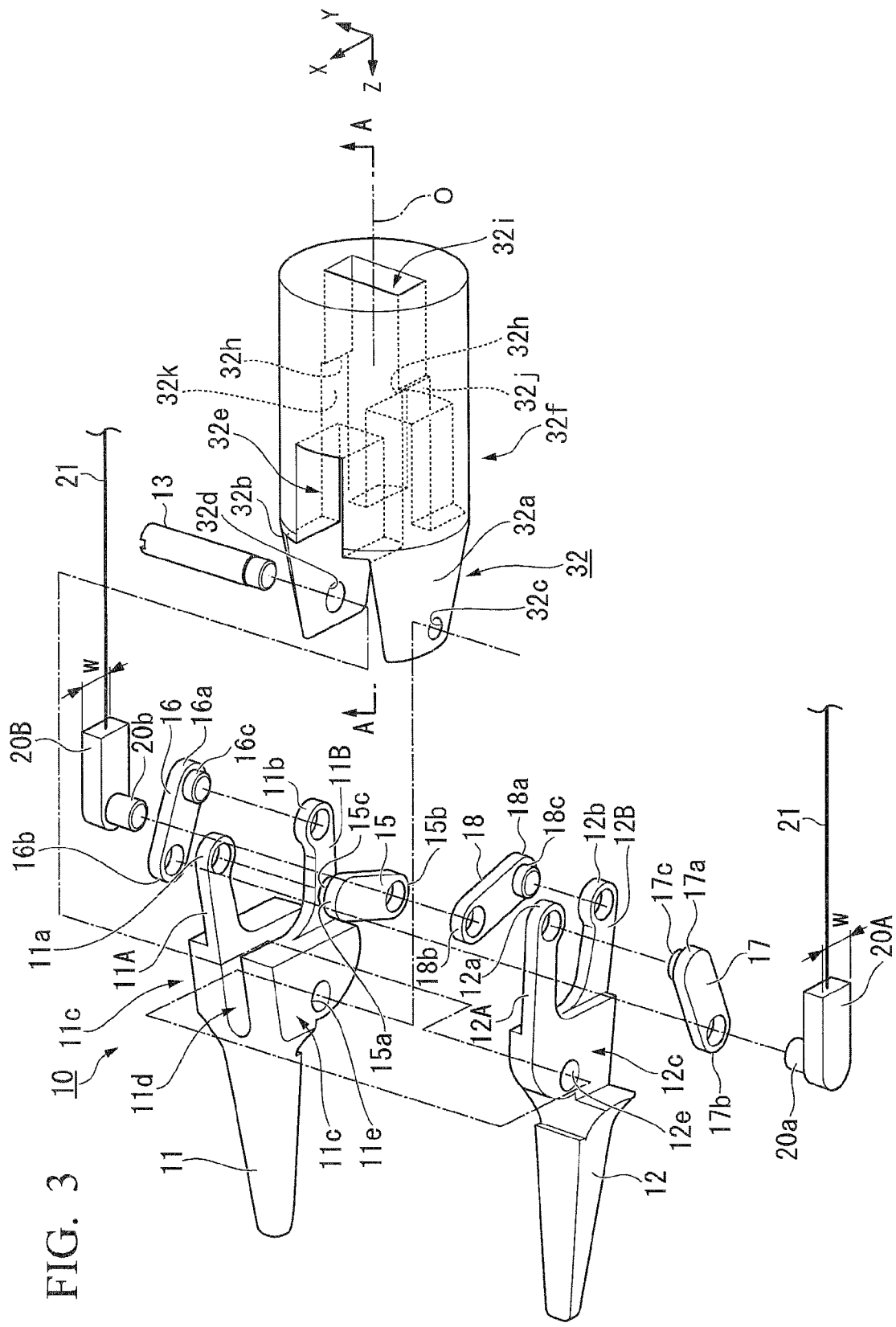
FIG. 3 is a schematic exploded perspective view of the tip end of the medical treatment tool of the first embodiment of the present invention.
Figure 4:
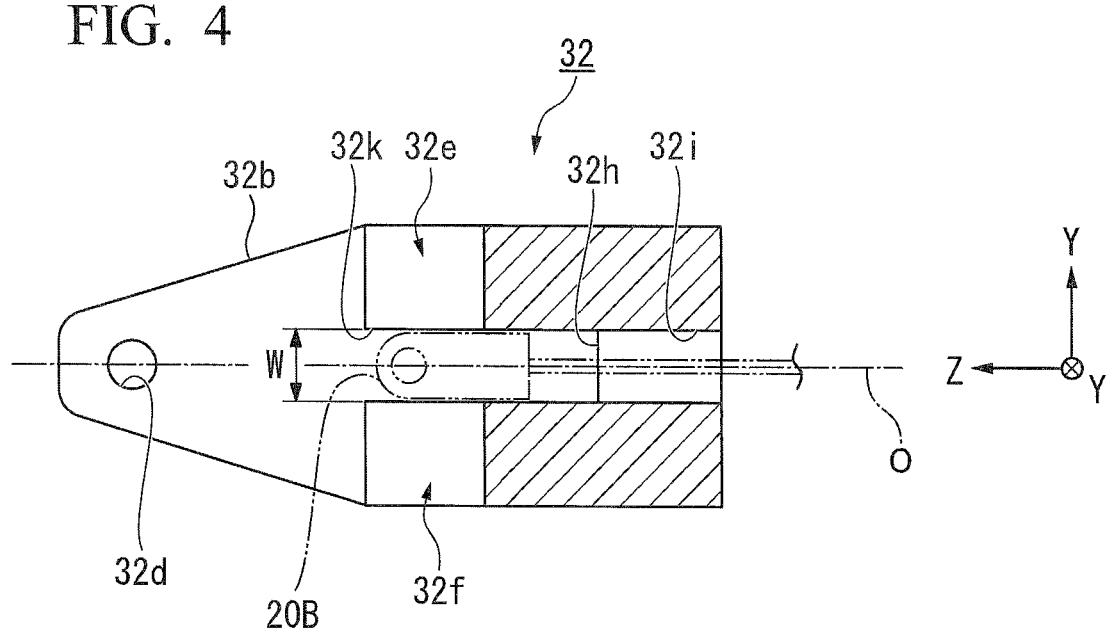
FIG. 4 is a cross-sectional view taken along A-A in FIG. 3.
Figure 5:
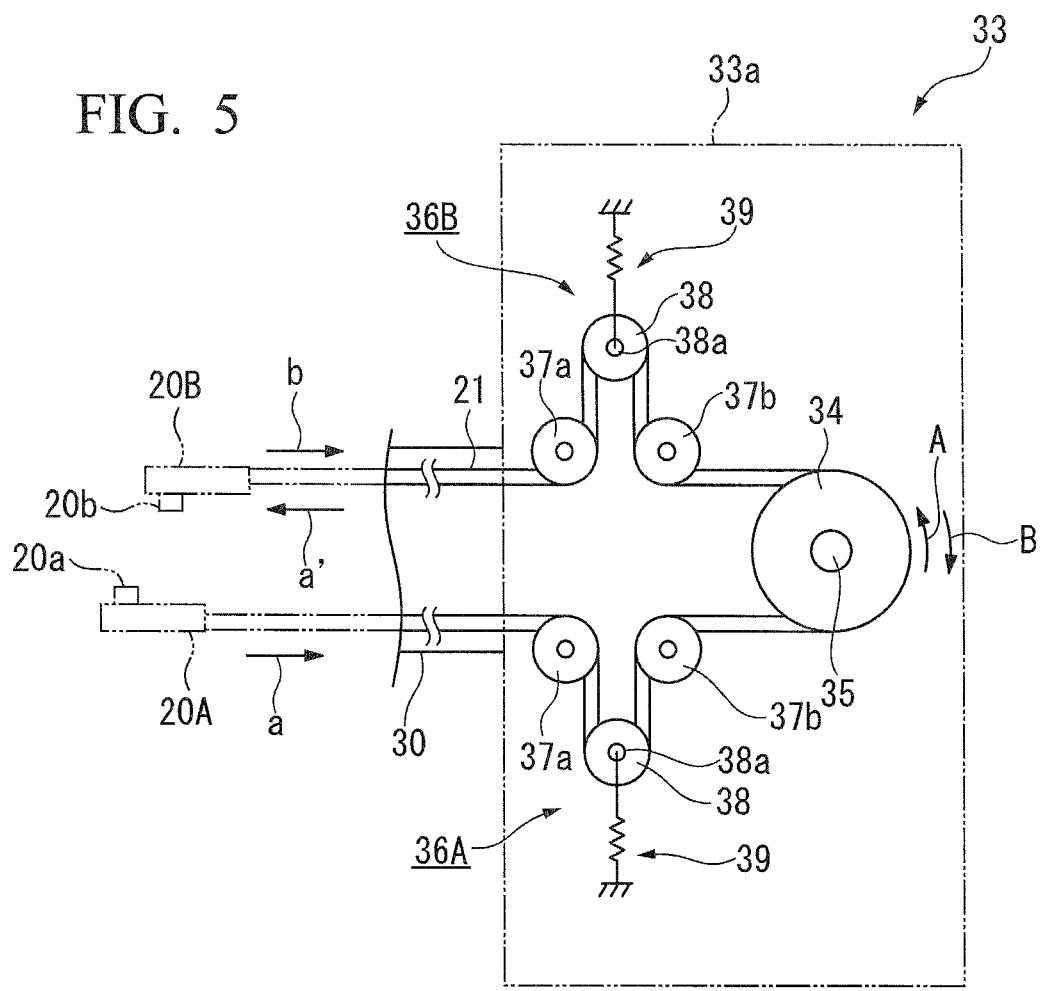
FIG. 5 is a schematic front view showing an example of a wire driving part used for opening and closing of a treatment section of the medical treatment tool of the first embodiment of the present invention.

FIG. 2A is a schematic front view showing a tip end of a medical treatment tool of a first embodiment of the present invention. FIG. 2B is a schematic cross-sectional view showing the tip end of the medical treatment tool of the first embodiment of the present invention. FIG. 3 is a schematic exploded perspective view of the tip end of the medical treatment tool of the first embodiment of the present invention. FIG. 4 is a cross-sectional view taken along A-A in FIG. 3. FIG. 5 is a schematic front view showing an example of a wire driving part used for opening and closing of a treatment section of the medical treatment tool of the first embodiment of the present invention.

A treatment tool 1 (medical treatment tool) can be mounted on the slave arms 200a to 200d as the above-described treatment tools 240a to 240d.

The treatment section 10, as shown in FIGS. 2A, 2B, and 3, is schematically configured to include a treatment tool 1 for performing various treatments, a manipulating member 20A (first manipulating member) for manipulating the treatment section 10, a manipulating member 20B (second manipulating member) (refer to FIG. 3), a wire 21 (refer to FIGS. 2B and 3) that tows the manipulating members 20A and 20B, and a sheath part 30 (refer to FIGS. 2A and 2B) through which the manipulating members 20A and 20B are inserted.

The treatment section 10 includes a pair of forceps pieces (treatment tool pieces) having a first forceps piece (first treatment tool pieces) 11 and a second forceps piece (second treatment tool pieces) 12. The first forceps piece 11 and the second forceps piece 12 are mutually rotatably coupled by a forceps rotation shaft 13 passed through holes 11e and 12e (refer to FIG. 3) that are respectively provided at intermediate portions thereof in the longitudinal direction, and a region closer to the tip end side than the forceps rotation shaft 13 is a forceps part 14 that is opened and closed to grasp, push open, or press down objects, such as a body tissue or a surgical instrument.

Additionally, the treatment section 10 includes a cover member 32 (substrate) that fixes the forceps rotation shaft 13, covers the base end side (side opposite to the forceps part 14) of the first forceps piece 11 and the second forceps piece 12 from the side, and couples the sheath part 30.

An intermediate portion (base end side) of the first forceps piece 11 in the longitudinal direction, as shown in FIG. 3, is provided with base portions 11c that face each other with a space 11d in the axial direction of the forceps rotation shaft 13 and that have through holes 11e that allows the forceps rotation shaft 13 to pass therethrough. Two arm portions 11A and 11B extend toward the base end side from the respective base portions 11c.

A through hole is provided at an end 11a of the arm portion 11A on the base end side, and a link rotation shaft 15c that is provided at a tip end 15a (first end) of a link member 15 (second link member) is inserted through this through hole. Thereby, the link member 15 is rotatably coupled to the arm portion 11A.

Additionally, a through hole is provided at an end 11b of the arm portion 11B on the base end side, and a link rotation shaft 16c that is provided at a tip end 16a (first end) of a link member 16 (first link member) is inserted through this through hole. Thereby, the link member 16 is rotatably coupled to the arm portion 11B.

The respective central axes of the link rotation shafts 15c and 16c are all parallel to the central axis of the forceps rotation shaft 13.

In this way, the arm portions 11A and 11B and the link members 15 and 16 are links of link mechanisms, respectively, and the link rotation shafts 15c and 16c that are rotary joints of the link mechanisms are provided at the ends 11a and 11b and the tip ends 15a and 16a. For this reason, in the present specification, the positions of the tip ends 15a and 16a that are ends of the link members and the ends 11a and 11b indicate the positions of the rotation centers of the rotary joints of the tip ends 15a and 16a, that is, the positions of the rotation centers of the link rotation shafts 15c and 16c, unless explicitly stated.

Additionally, this is also the same in the positions of the ends of other links to be described below.

Similarly, an intermediate portion (base end side) of a second forceps piece 12 in the longitudinal direction is provided with a base portion 12c that can be inserted into the space 11d of the first forceps piece 11 and that has a through hole 12e that allows the forceps rotation shaft 13 to pass therethrough. Two arm portions 12A and 12B extend toward the base end side from the base portion 12c.

The base portion 12c of the second forceps piece 12 is inserted into the space 11d of the first forceps piece 11. The second forceps piece is rotatably coupled to the forceps rotation shaft 13 together with the first forceps piece 11 in a state where the forceps rotation shaft 13 has passed through the respective through holes 11e and the through hole 12e.

A through hole is provided at an end 12a of the arm portion 12A on the base end side, and a link rotation shaft 17c that is provided at a tip end 17a (first end) of a link member 17 (first link member) is inserted through this through hole. Thereby, the link member 17 is rotatably coupled to the arm portion 12A.

Additionally, a through hole is provided at an end 12b of the arm portion 12B on the base end side, and a link rotation shaft 18c that is provided at a tip end 18a (first end) of a link member 18 (second link member) is inserted through this through hole. Thereby, the link member 18 is rotatably coupled to the arm portion 12A.

The respective central axes of the link rotation shafts 17c and 18c are all parallel to the central axis of the forceps rotation shaft 13. Additionally, the respective tip ends 17a and 18a of the respective link members 17 and 18 are coupled closer to the base end side than the forceps rotation shaft 13 in the first forceps piece 11.

The base ends 15b and 18b (second ends) of the link members 15 and 18 are rotatably connected to the manipulating member 20B via a connection rotation shaft 20b (to be described below) of the manipulating member 20B. The central axis of the connection rotation shaft 20b is parallel to the respective central axes of the forceps rotation shaft 13 and the link rotation shafts 15c and 18c, and the respective link members 15 and 18 are rotatable relative to the manipulating member 20B.

The base ends 16b and 17b (second ends) of the link members 16 and 17 are rotatably connected to the manipulating member 20A via a connection rotation shaft 20a (to be described below) of the manipulating member 20A. The central axis of the connection rotation shaft 20a is parallel to the respective central axes of the forceps rotation shaft 13 and the link rotation shafts 16c and 17c, and the respective link members 16 and 17 are rotatable relative to the manipulating member 20A.

The manipulating member 20A is formed from metal or the like and the connection rotation shaft 20a that rotationally supports the base ends 16b and 17b is provided on the tip end side of the manipulating member 20A. In the present embodiment, the shape of the manipulating member 20A is, for example, a block-shaped member of a rectangular cross-section that is rounded in the shape of a semicircle on the tip end side directed to the forceps part 14 side and is horn-shaped on the base end side. The width in a direction orthogonal to the connection rotation shaft 20a with respect to a direction that goes from the base end side of the manipulating member 20A to the tip end side is set to w.

One end of the wire 21 is inserted into the base end of the manipulating member 20A, and one end of the wire 21 is integrally connected by welding, adhesion, or caulking.

The manipulating member 20B is formed from metal or the like and the connection rotation shaft 20b that rotationally supports the base ends 15b and 18b is provided on the tip end side of the manipulating member 20B. In the present embodiment, the shape of the manipulating member 20B is, for example, a block-shaped member of a rectangular cross-section that is rounded in the shape of a semicircle on the tip end side directed to the forceps part 14 side and is horn-shaped on the base end side. The width in a direction orthogonal to the connection rotation shaft 20b with respect to a direction that goes from the base end side of the manipulating member 20B to the tip end side is set to w.

The other end of the wire 21 is inserted into the base end of the manipulating member 20B, and the other end of the wire 21 is integrally connected by welding, adhesion, or caulking.

From such a configuration, the first forceps piece 11, the second forceps piece 12, and the link members 15, 16, 17, and 18 constitute link mechanisms that have the forceps rotation shaft 13, the link rotation shafts 15c, 16c, 17c, and 18c, and the connection rotation shafts 20a and 20b as a rotary joint. For this reason, when describing the link mechanisms, the first forceps piece 11, the second forceps piece 12, and the link members 15, 16, 17, and 18 may be collectively referred to as link member.

In the present embodiment, a case where the lengths of respective pairs of the arm portion 11A and the arm portion 12B, the arm portion 11B and the arm portion 12A, the link member 15 and the link member 18, and the link member 16 and the link member 17 are set to the same lengths, respectively, and link mechanisms symmetrical with respect to the center of opening and closing center are configured will be described as an example.

The wire 21 is a member that transmits the manipulation force that advances and retracts the manipulating members 20A and 20B to the manipulating members 20A and 20B, and includes a metallic stranded wire in the present embodiment.

One end and the other end of the wire 21 are fixed to the base ends of the manipulating members 20A and 20B, respectively.

The cover member 32, as shown in FIG. 3, has side plate portions 32a and 32b that cover a base-end-side portion of the forceps part 14 from the side on the tip end side, has an outer shape that is columnar on the base end side, and is a member made of, for example, metal or the like. A through hole 32i that has a rectangular cross-section along the central axis O of the columnar portion is provided inside the cover member 32.

In the following, when referring to relative directions in the treatment section 10, as shown in FIG. 3, the XYZ coordinate system in which an axis that coincides with the central axis O is the Z-axis, a direction orthogonal to the Z-axis and parallel to the central axis of the forceps rotation shaft 13 is the Y-axis, and an axis orthogonal to the Y-axis and the Z-axis is the X-axis may be used.

The positive direction of the Z-axis is a direction that goes to the tip end side in the treatment section 10, and the negative direction of the Z-axis is a direction that goes to the base end side in the treatment section 10.

In the present embodiment, symmetry planes in the cover member 32 are a YZ plane and a ZX plane, and the side plate portions 32a and 32b have a shape that is plane-symmetrical with respect to the YZ plane and the ZX plane.

The ends of the side plate portions 32a and 32b on the tip end side are respectively provided with shaft fixing portions 32c and 32d including through holes for inserting the forceps rotation shaft 13 coupling the first forceps piece 11 and the second forceps piece 12 and fixing the position thereof.

Additionally, a groove portion 32e that rotatably accommodates the arm portions 11A and 12A and the link members 15 and 16 of the first forceps piece 11 and the second forceps piece 12 that are coupled by the forceps rotation shaft 13 between the side plate portions 32a and 32b, and a groove portion 32f that rotatably accommodates the arm portions 11B and 12B and the link members 17 and 18 are provided through the X-axis direction at the positions along the ZX plane on the tip end side of the columnar portion to which the side plate portions 32a and 32b are fixed.

For this reason, as shown in FIG. 2A, in an assembled state, the forceps rotation shaft 13 is fixed to the cover member 32 and the first forceps piece 11 and the second forceps piece 12 are rotatably supported with respect to the cover member 32.

The interval on the tip end side of the inner peripheral surfaces of the through holes 32i that face each other in the Y-axis direction is made wider than the intervals on the base end side thereof. For this reason, stepped portions 32h are respectively formed at the same positions of intermediate portions in the Z-axis direction.

Additionally, a guide groove portion 32j (first guide) and a guide groove portion 32k (second guide) are respectively formed in the inner peripheral surfaces of the through holes 32i that face each other in the X-axis direction closer to the tip end side than the stepped portions 32h, respectively. The guide groove portion 32j and the guide groove portion 32k have a slightly larger width W (refer to FIG. 4) than the width w of the manipulating members 20A and 20B, and hold the manipulating members 20A and 20B so as to be capable of advancing and retracting in the Z-axis direction.

Thereby, if the manipulating member 20A (20B) is driven along the Z-axis direction by the wire 21, the manipulating member 20A (20B) can be smoothly advanced and retracted in the Z-axis direction with the guide groove portion 32j (32k) as a guide.

The sheath part 30, as shown in FIGS. 2A and 2B, includes a sheath 31 that is formed in a tubular shape, and the wire 21 is inserted into the sheath 31 so as to be capable of advancing and retracting. In the present embodiment, a well-known coiled sheath having flexibility is used as the sheath 31.

A tip end of the sheath 31 is attached to the inside of a base end supporting portion 32g provided on the base end side of the cover member 32. Thereby, the forceps rotation shaft 13 is fixed so as not to move with respect to the sheath part 30.

As shown in FIG. 5, a wire driving part 33 is coupled to the base end of the sheath part 30 opposite to the side where the cover member 32 is connected.

The wire driving part 33 is detachably connected to an adapter in which a rotating mechanism is provided as a driving mechanism, among the adapters 220a to 220d of FIG. 1. Additionally, the wire driving part 33 is a member that transmits the power supplied from a slave arm corresponding to the connected adapter to the wire 21. In the following, a case where the wire driving part 33 is mounted on an adapter 220a and receives the power from a slave arm 200a will be described as an example.

As for the schematic configuration of the wire driving part 33, in the present embodiment, a drive shaft 35, a drive pulley 34, and tension application portions 36A and 36B are provided inside a housing 33a that has such a shape that the housing is attachable to and detachable from the adapter 220a.

When the drive shaft 35 is rotatably held by the housing 33a and the housing 33a is mounted on the adapter 220a, an end (not shown) is configured to be capable of being coupled to a power transmission shaft (not shown) of the adapter 220a. The end (shown in FIG. 5) of the drive shaft 35 is fixed to the drive pulley 34.

The drive pulley 34 is fixed to the end of the drive shaft 35, rotates with the rotation of the drive shaft 35, and is wound around an intermediate portion of the wire 21 stretched between the manipulating members 20A and 20B from the inside of a wiring path of the wire 21.

The tension application portion 36A applies tension to the wire 21 at a position between the manipulating member 20A and the drive pulley 34. The tension application portion 36B is a position between the manipulating member 20B and the drive pulley 34, and adds tension to a wire 21.

Additionally, the tension application portions 36A and 36B includes fixed pulleys 37a and 37b, a tension pulley 38, and a spring 39 in common, respectively. The differences between the tension application portion 36A and the tension application portion 36B are only the installation positions of these portions with respect to the wire 21.

The fixed pulleys 37a and 37b are rotatably fixed to the ends of supporting members (not shown) at mutually separated positions, outside the wiring path of the wire 21 stretched between the manipulating member 20A (20B) and the drive pulley 34.

The tension pulley 38 is wound around the wire 21 stretched between the fixed pulleys 37a and 37b from the inside of the wiring path of the wire 21, and pulls out the wire 21 toward the outside of the wiring path. In the present embodiment, the tension pulley 38 is rotatably attached to the rotation shaft 38a that is resiliently supported by the housing 33a via a spring 39.

The configuration of the spring 39 is not particularly limited if the rotation shaft 38a can be resiliently supported, and for example, appropriate spring members, such as a coiled spring and a flat spring, or a resilient member can be adopted.

With respect to the operation when the treatment tool 1 configured as described above is used, a case where the treatment tool is attached to one of the above-described slave arms 200a to 200d, for example, the slave arm 200a will be described as an example.

Figure 6:
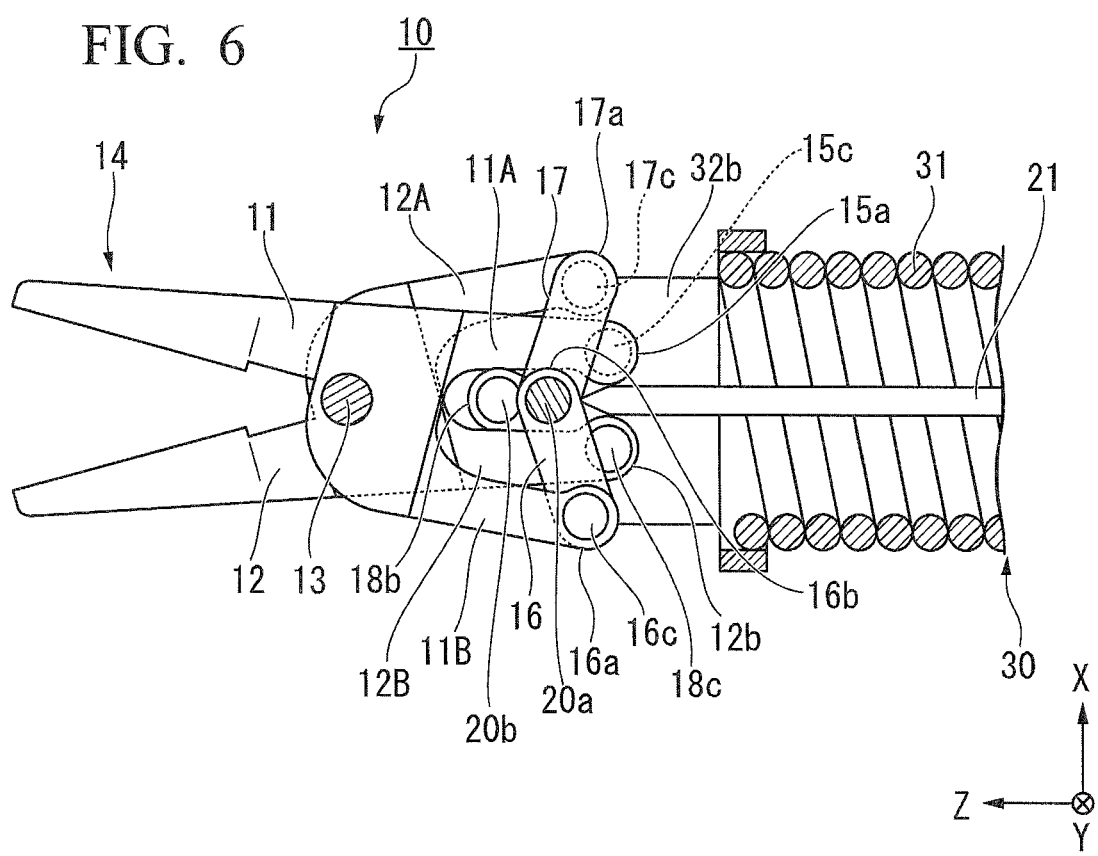
FIG. 6 is a schematic cross-sectional view showing a state where the treatment section of the medical treatment tool of the first embodiment of the present invention is opened.
Figure 8A:
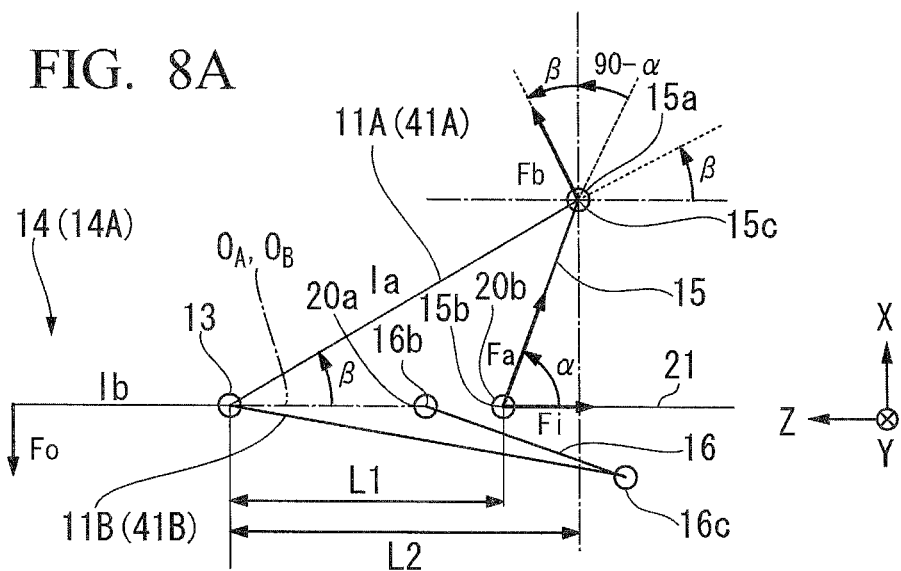
FIG. 8A is a schematic view for describing an opening and closing action in a toggle mechanism of the medical treatment tool of the first embodiment of the present invention.
Figure 8B:
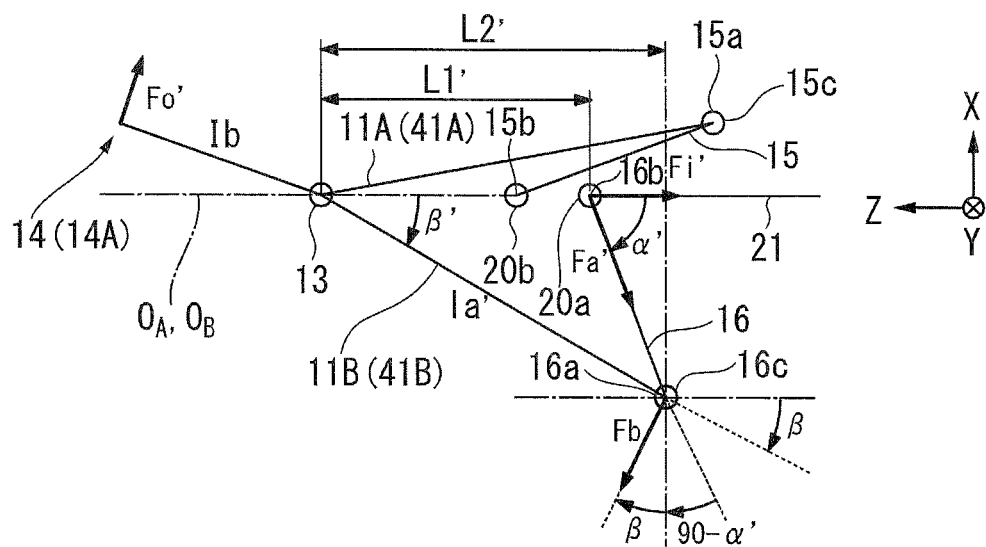
FIG. 8B is a schematic view for describing the opening and closing action in the toggle mechanism of the medical treatment tool of the first embodiment of the present invention.

FIG. 6 is a schematic cross-sectional view showing a state where the treatment section of the medical treatment tool of the first embodiment of the present invention is opened. FIGS. 7A and 7B are schematic views showing the positional relationship between the link members when the treatment section of the medical treatment tool of the first embodiment of the present invention is closed. FIGS. 7C and 7D are schematic views showing the positional relationship between the link members when the treatment section of the medical treatment tool of the first embodiment of the present invention is opened. FIGS. 8A and 8B are schematic views for describing an opening and closing action in a toggle mechanism of the medical treatment tool of the first embodiment of the present invention.

First, an operator Op mounts the wire driving part 33 of the treatment tool 1 on an adapter 220a of a desired slave arm, for example, the slave arm 200a. This connects the treatment tool 1 and the slave arm 200a. Additionally, the treatment tools 240b to 240d that are other treatment tools are connected to the adapters 220b to 220d if needed.

If the operator Op performs predetermined manipulation on the corresponding master arm, a power unit of the slave arm is driven via the slave control circuit 400a. The power generated in this power unit is converted into a linear-motion motion or a rotary motion via an adapter.

For example, the power of the slave arm 200a that drives the treatment tool 1 is converted into a rotary motion in the adapter 220a, and the drive shaft 35 of the wire driving part 33 is rotated according to the degree of movement.

In the present embodiment, if the drive pulley 34 is rotated in the shown counterclockwise direction (the direction of arrow A) in FIG. 5, the manipulating member 20A is towed to the drive pulley 34 side by the wire 21 on the manipulating member 20A side (refer to arrow a). Additionally, the wire 21 on the manipulating member 20B side is fed out to the manipulating member 20B side from the drive pulley 34.

On the contrary, if the drive pulley 34 is rotated in the clockwise direction (the direction of arrow B), the manipulating member 20B is towed to the drive pulley 34 side by the wire 21 on the manipulating member 20B side (refer to arrow b). Additionally, the wire 21 on the manipulating member 20A side is fed out to the manipulating member 20A side from the drive pulley 34.

If the manipulating members 20A and 20B are towed in this way, the respective link members in the treatment tool 1 move according to the respective degrees of movement, and an opening and closing action is performed between a state (refer to FIG. 2B) where the forceps part 14 is closed at an opening angle of 0° and a state (refer to FIG. 6) where the forceps part is opened at a maximum opening angle.

For this reason, the manipulating member 20A is a first manipulating member that is provided so as to be movable along a given advance and retraction direction with respect to the cover member 32 and transmits a manipulation force caused by the towing of rotating the first forceps piece 11, and the second forceps piece 12 in the opening direction.

Additionally, the manipulating member 20B is a second manipulating member that is provided so as to be movable along a given advance and retraction direction with respect to the cover member 32 and transmits a manipulation force caused by the towing of rotating the first forceps piece 11, and the second forceps piece 12 in a closing direction.

Hereinafter, straight lines formed by the movement tracks of points on the central axes of the connection rotation shafts 20a and 20b during advance and retraction of the manipulating members 20A and 20B are referred to as "advance and retraction axes of the base ends" of the respective link members connected to the manipulating members 20A and 20B that advance and retract with this movement.

In the present embodiment, the advance and retraction axis $O_A$ (refer to FIGS. 7B and 7D) of the base ends 16b and 17b passes through the central axis of the forceps rotation shaft 13 and the central axis of the connection rotation shaft 20a, and is parallel to the central axis O of the cover member 32. Additionally, the advance and retraction axis $O_A$ is also parallel to the central axis of the guide groove portion 32j along the longitudinal direction.

Additionally, the advance and retraction axis $O_B$ (refer to FIGS. 7A and 7C) of the base ends 15b and 18b passes through the central axis of the forceps rotation shaft 13 and the central axis of the connection rotation shaft 20b, and is parallel to the central axis O of the cover member 32. Additionally, the advance and retraction axis $O_B$ is also parallel to the central axis of the guide groove portion 32k along the longitudinal direction.

First, the positional relationship among the respective members in the treatment tool 1 in a state where the forceps part 14 is closed will be described.

In a state where the forceps part 14 is closed, as shown in FIG. 7A, the tip ends of the first forceps piece 11 and the second forceps piece 12 are closed in close contact with each other. On the base end side, the end 11a of the arm portion 11A and the end 12b of the arm portion 12B are in the state of being furthest separated from each other in the circumferential direction of the rotation around the forceps rotation shaft 13. Additionally, at this time, as shown in FIG. 7B, the end 11b of the arm portion 11B and the end 12a of the arm portion 12A are in the state of closest approach to each other in the circumferential direction of the rotation around the forceps rotation shaft 13.

In the present embodiment, this closed state, as shown in FIG. 7A, is realized by positioning the connection rotation shaft 20b at a position distant by more than a given distance from the forceps rotation shaft 13 in a movable range on the advance and retraction axis $O_B$. That is, as the link member 15 is rotated in the shown counterclockwise direction around the link rotation shaft 15c from the open state and the link member 18 is rotated in the shown clockwise direction around the link rotation shaft 18c, the connection rotation shaft 20b and the link rotation shafts 15c and 18c approaching each other to within less than a given distance in the Z-axis direction is realized.

Additionally, at this time, as shown in FIG. 7B, the connection rotation shaft 20a is positioned at a position where the connection rotation shaft has approached the forceps rotation shaft 13 to within less than a given distance in a movable range on the advance and retraction axis $O_A$, and the connection rotation shaft 20a and the link rotation shafts 16c and 17c are separated from each other more than a given distance in the Z-axis direction.

For this reason, in a state where the forceps part 14 is closed, the connection rotation shaft 20a is at a position nearest to the forceps rotation shaft 13 or is in proximity to this position, in the movable range within the guide groove portion 32j. Additionally, the connection rotation shaft 20b is at a position farthest from to the forceps rotation shaft 13 or is in proximity to this position, in the movable range within the guide groove portion 32k.

The position of the stepped portion 32h on the Y-axis positive side formed in the cover member 32 specifies the movement range of the manipulating member 20B to the base end side, and the stepped portion 32h functions as a stopper that regulates the maximum retraction amount of the manipulating member 20B. The position of the stepped portion 32h is set in consideration of the shape of an object to be grasped and the above yield stress. Therefore, even if the base end of the manipulating member 20B is retracted to the stepped portion 32h in a state where an object is grasped, the respective link members 15 and 18, the first forceps piece 11 and the second forceps piece 12 do not cause plastic deformation.

In order to open the forceps part 14 from such a state that the forceps part 14 closed, the operator Op manipulates a master arm to thereby transmit power to the drive shaft 35 of the wire driving part 33 from the slave arm 200a and to rotate the drive pulley 34 of the wire driving part 33 in the direction of arrow A of FIG. 5. Thereby, the wire 21 between the manipulating member 20A and the drive pulley 34 is towed in the direction of arrow a of FIG. 5, and the manipulating member 20A is moved to the drive pulley 34 side.

In this case, although the manipulating member 20A retracts to the sheath part 30 side, the forceps rotation shaft 13 does not retract to the sheath part 30 side because the forceps rotation shaft is fixed to the cover member 32. As a result, as shown in FIG. 7D, the connection rotation shaft 20a moves away from the forceps rotation shaft 13. Along with this, as the connection rotation shaft 20a and the link rotation shafts 16c and 17c approach each other in the Z-axis direction, the link members 16 and 17 rotate with respect to the first forceps piece 11, the second forceps piece 12, and the manipulating member 20A, and the forceps part 14 is opened.

On the other hand, although the wire 21 between the manipulating member 20B and the drive pulley 34 is fed out in a direction separated from the drive pulley 34 as shown by arrow a' of FIG. 5, since a sagging side is in this direction, the tension of the wire 21 tends to decrease.

However, since the manipulating member 20B is coupled to the arm portions 11A and 12B rotated around the forceps rotation shaft 13 via the link members 15 and 18 similarly to the arm portions 11B and 12A and is interlocked with the movement of a link mechanism, the manipulating member moves in the direction of arrow a' of FIG. 5 even if there is no action from the wire 21.

For this reason, although the tension of the wire 21 has no great change before the start of towing, the tension of the wire 21 changes due to influences, such as elongation deformation of the wire 21, the movement errors of the link mechanism, and deformation of the links. In the present embodiment, the tension application portion 36B is provided between the manipulating member 20B and the drive pulley 34. For this reason, even if the tension of the wire 21 tends to change, the tension of the wire 21 is kept constant since the tension pulley 38 moves according to changes in tension and the resilient restoration force of the spring 39 acts.

If the connection rotation shaft 20a is towed at the maximum to the Z-axis negative side, as shown in FIG. 7D, on the base end side of the first forceps piece 11 and the second forceps piece 12, the end 12a of the arm portion 12A and the end 11b of the arm portion 11B are furthest separated from each other in the circumferential direction of the rotation around the forceps rotation shaft 13, and the forceps part 14 is furthest opened. Additionally, at this time, as shown in FIG. 7C, the end 11a of the arm portion 11A and the end 12b of the arm portion 12B are in the state of closest approach to each other in the circumferential direction of the rotation around the forceps rotation shaft 13.

Additionally, for example, if the operator Op manipulates a master arm to rotate the drive pulley 34 in the direction of arrow B of FIG. 5, through the operation contrary to the above described one, the manipulating member 20A is towed to the drive pulley 34 side and is moved in the direction of arrow b of FIG. 5 to close the forceps part 14.

At this time although the wire 21 between the manipulating member 20A and the drive pulley 34 becomes the sagging side contrary to the above-described one, in the present embodiment, the tension application portion 36A is provided between the manipulating member 20A and the drive pulley 34. For this reason, even if the tension of the wire 21 tends to change, the tension of the wire 21 is kept constant since the tension pulley 38 moves according to changes in tension and the resilient restoration force of the spring 39 acts.

In this way, in the treatment tool 1, the manipulating member 20A is towed whereby the pair of treatment tool pieces is turned and the forceps part 14 is opened, and the manipulating member 20B is towed whereby the pair of treatment tool pieces is rotated and the forceps part 14 is closed. For this reason, according to the treatment tool 1, desired procedures, such as grasping a target tissue or grasping tools required for treatment, such as a curved needle or suture thread can be performed.

Additionally, when the manipulating members 20A and 20B are moved to perform the opening and closing action of the forceps part 14, the treatment tool 1 can perform manipulation simply by towing the wire 21 without using a rod. Therefore, the flexibility of the sheath part 30 can be enhanced.

In the present embodiment, as shown in FIG. 7A, the connection rotation shaft 20b is located closer to the tip end (forceps rotation shaft 13 side) than the link rotation shafts 15c and 18c in a state where the forceps part 14 is closed. That is, the base ends 15b and 18b of the link members 15 and 18 are located closer to the tip end side than the tip ends 15a and 18a.

Additionally, the distance between the advance and retraction axis $O_B$ of the base end 15b of the link member 15 and the link rotation shaft 15c is shorter than the length of the link member 15. Similarly, the distance between the advance and retraction axis $O_B$ of the base end 18b and the link rotation shaft 18c is shorter than the length of the link member 18.

For this reason, as shown in FIG. 8A, the length L1 when a line segment connecting the rotation center (central axis of the forceps rotation shaft 13) of a pair of treatment tool pieces and the position (the center position of the connection rotation shaft 20b in the ZX plane) of the base end 15b of the link member 15 is projected on the advance and retraction axis $O_B$ of the base end 15b is set so as to become shorter than the length L2 when a line segment of length la connecting the rotation center and the position (the center position of the link rotation shaft 15c in the ZX plane) of the tip end 15a of the link member 15 is projected on the advance and retraction axis $O_B$ of the base end. In the present embodiment, the length L1 is equal to the distance between the rotation center of the treatment tool pieces and the base end 15b of the link member 15. The details of FIG. 8A will be described below.

Additionally, although not particularly shown, the same relationship is also satisfied in the positional relationship among the forceps rotation shaft 13, the tip end 18a, and the base end 18b from the symmetric property of the link mechanisms in the present embodiment about the central axis of the opening and closing.

Additionally, in the present embodiment, as shown in FIG. 7D, the connection rotation shaft 20a is located closer to the tip end side (forceps rotation shaft 13 side) than the link rotation shafts 16c and 17c in a state where the forceps part 14 is opened. That is, the base ends 16b and 17b of the link members 16 and 17 are located closer to the tip end side than the tip ends 16a and 17a.

Additionally, the distance between the advance and retraction axis $O_A$ of the base end 16b of the link member 16 and the link rotation shaft 16c is shorter than the length of the link member 16. Similarly, the distance between the advance and retraction axis $O_A$ of the base end 17b and the link rotation shaft 17c is shorter than the length of the link member 17.

For this reason, as shown in FIG. 8B, the length L1' when a line segment connecting the rotation center (central axis of the forceps rotation shaft 13) of a pair of treatment tool pieces and the position (the center position of the connection rotation shaft 20a in the ZX plane) of the base end 16b of the link member 16 is projected on the advance and retraction axis $O_A$ of the base end 16b is set so as to become shorter than the length L2' when a line segment of length la' connecting the rotation center and the position (the center position of the link rotation shaft 16c in the ZX plane) of the tip end 16a of the link member 16 is projected on the advance and retraction axis $O_A$ of the base end. In the present embodiment, the length L1' is equal to the distance between the rotation center of the treatment tool pieces and the base end 16b of the link member 16. The details of FIG. 8B will be described below.

Additionally, although not particularly shown, the same relationship is also satisfied in the positional relationship among the forceps rotation shaft 13, the tip end 17a, and the base end 17b from the symmetric property of the link mechanisms in the present embodiment about the central axis of the opening and closing.

From such a configuration, the manipulating members 20A and 20B, the link members 15, 16, 17, and 18, the first forceps piece 11, and the second forceps piece 12 constitute a so-called toggle mechanism.

In the toggle mechanism, an opening and closing action can be easily performed even by a small manipulation force. This point will be described below with reference to FIG. 8A and FIG. 8B.

The first forceps piece 11, the forceps rotation shaft 13, the link members 15 and 16, the link rotation shafts 15c and 16c, the connection rotation shafts 20a and 20b, and the wire 21 are schematically shown in FIGS. 8A and 8B.

As shown in FIG. 8A, if a manipulation input Fi is made to act on the wire 21 to tow the connection rotation shaft 20b in the Z-axis negative direction, the connection rotation shaft 20b retracts, and the angle α formed by the advance and retraction axis $O_B$ and the link member 15 on the base end side becomes large. A force Fb that moves the link rotation shaft 15e in the direction separated from the advance and retraction axis $O_B$ is generated. The force Fb acts so as to rotate the first forceps piece 11 in the counter-clockwise direction when seen in the positive direction from the Y-axis negative direction around the forceps rotation shaft 13. Finally, an output Fo is generated in the forceps part 14.

la and lb shown in FIG. 8A represent the length of the region closer to the tip end side than the forceps rotation shaft 13 and the length of the arm portion 11A closer to the base end side than the forceps rotation shaft 13 in the first forceps piece 11, and the angle β represents an angle formed by the advance and retraction axis $O_B$ and a straight line connecting the forceps rotation shaft 13 and the link rotation shaft 15c. Additionally, although the second forceps piece 12 or the like is not shown, the output Fo is similarly generated.

The magnitude of the output Fo that is generated at the forceps part 14 in the first forceps piece 11 and the second forceps piece 12 is expressed by the following Formula (1). Here, α and β are the angles expressed in units of degrees (°).

[Formula 1]

$$Fo = \frac{Fi \cdot la \cdot \cos(90 - \alpha + \beta)}{2 \cdot lb \cdot \cos(\alpha)} \qquad (1)$$

Accordingly, the output Fo becomes exponentially larger as the angle α approaches 90°. The output Fo can be theoretically made infinite. However, actually, if the output Fo becomes more than a predetermined magnitude, the respective link members 15 and 17 or the first forceps piece 11 and the second forceps piece 12 deform plastically. Therefore, the upper limit of the grasping force is defined by the yield stress of these members.

Additionally, the point that an opening force caused by the action of the toggle mechanism can be increased when the forceps part 14 is opened will be described similarly to the above.

As shown in FIG. 8B, if a manipulation input Fi' is made to act on the wire 21 and the connection rotation shaft 20a is towed in the Z-axis negative direction, the connection rotation shaft 20a retracts and the angle α' formed by the advance and retraction axis $O_A$ and the link member 15 on the base end side becomes large, and a force Fb' of moving the link rotation shaft 16c in a direction in which the link rotation shaft is separated from the advance and retraction axis $O_A$ is generated. The force Fb' acts so as to rotate the first forceps piece 11 in the clockwise direction when seen in the positive direction from the Y-axis negative direction around the forceps rotation shaft 13. In a case where an external force that inhibits the forceps part 14 from being opened acts, finally, output Fo' is generated in the forceps part 14.

In the first forceps piece 11, la' shown in FIG. 8B represents the length of the arm portion 11B closer to the tip end side than the forceps rotation shaft 13, and the angle β' represents an angle formed by the advance and retraction axis $O_A$ and a straight line connecting the forceps rotation shaft 13 and the link rotation shaft 16c. Additionally, although the second forceps piece 12 or the like is not shown, the output Fo' is similarly generated.

The magnitude of the output Fo' that is generated at the forceps part 14 in the first forceps piece 11 and the second forceps piece 12 is expressed by the following Formula (2). Here, α' and β' are the angles expressed in units of degrees (°).

[Formula 2]

$$Fo' = \frac{Fi' \cdot la' \cdot \cos(90 - \alpha' + \beta')}{2 \cdot lb \cdot \cos(\alpha')} \quad (2)$$

Accordingly, in a case where an external force that inhibits the forceps part 14 from being opened acts, the output Fo' becomes exponentially larger so that the angle α' approaches 90 degrees.

Similarly to the above, the stepped portion 32h on the side of the Y-axis negative direction, which is formed in the cover member 32, functions as a stopper that regulates the maximum retraction amount of the manipulating member 20A. The position of the stepped portion 32h is set in consideration of the external force that inhibits the forceps part 14 from being opened, and the yield stresses of the respective members of the treatment tool 1.

As described above, according to the treatment tool 1 of the present embodiment, the toggle mechanism is constituted by the first forceps piece 11, the second forceps piece 12, the respective link members 15, 16, 17, and 18, and the manipulating members 20A and 20B of the treatment section 10. For this reason, in a region where the link members 15 and 18 form an angle approximate to a right angle with the advance and retraction axis $O_B$ by towing manipulation and a region where the link members 16 and 17 forms an angle approximate a right angle with the advance and retraction axis $O_A$, an opening and closing force generated in the forceps part 14 is increased even by a relatively small manipulation input. For this reason, an opening and closing action can be efficiently performed even by a small manipulation force.

Particularly in a case where the forceps part 14 is closed, the grasping force generated in the forceps part 14 can be efficiently increased. For this reason, an object to be grasped can be efficiently pressurized or can be firmly grasped.

Additionally, in a case where the forceps part 14 is opened, the opening force generated in the forceps part 14 can be efficiently increased. For this reason, the forceps part can be smoothly opened against the external force that inhibits the opening. Additionally, the operation of pushing open, for example, a living body tissue or the like can be easily performed. Additionally, a state where the forceps part 14 is opened at the maximum can be stably maintained against the external force.

Accordingly, when the pair of treatment tool pieces is manipulated and opened and closed, the closing force can be increased in a case where the treatment tool pieces are closed and the opening force can be increased even in a case where the treatment tool pieces are opened.

Additionally, the reaction force of the output Fo acts on the connection rotation shafts 20b and 20a on which the manipulation inputs Fi and Fi' acts in the directions in which the advance and retraction axes $O_B$ and $O_A$ are separated from the link members 15, 18, 16, and 17. However, the link members 15 and 18 and the link members 16 and 17 of the present embodiment make a pair, respectively, and are arranged laterally symmetrically with respect to the advance and retraction axes $O_B$ and $O_A$.

For this reason, since the connection rotation shaft 20b is located in the middle of the link rotation shafts 15c and 18c and the connection rotation shaft 20a is located in the middle of the link rotation shafts 16c and 17c, the reaction force of the output Fo and the reaction force of the output Fo' that act on the connection rotation shafts 20b and 20a, respectively, act in opposite directions. As a result, the reaction forces are cancelled out and become zero.

Accordingly, the manipulating members 20A and 20B accommodated in the guide groove portions 32j and 32k are not strongly pressed against the inner surfaces of the guide groove portions 32j and 32k, respectively, and generation of large friction is suppressed.

[Second Embodiment]

Figure 9A:
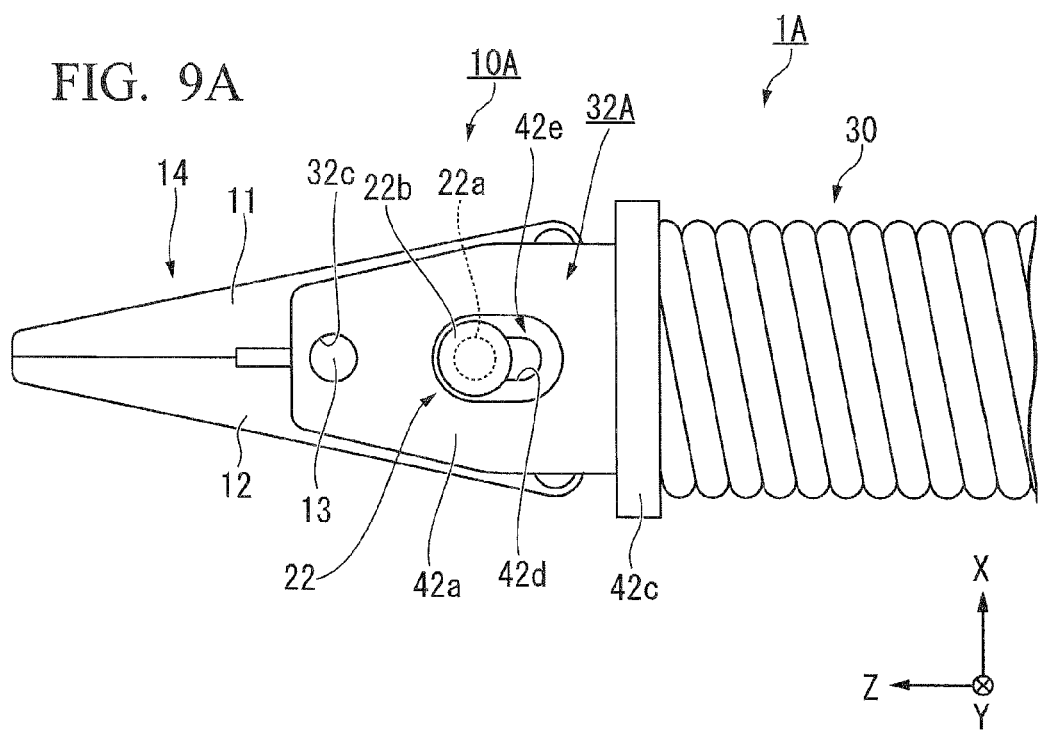
FIG. 9A is a schematic front view showing a tip end of a medical treatment tool of a second embodiment of the present invention.
Figure 9B:
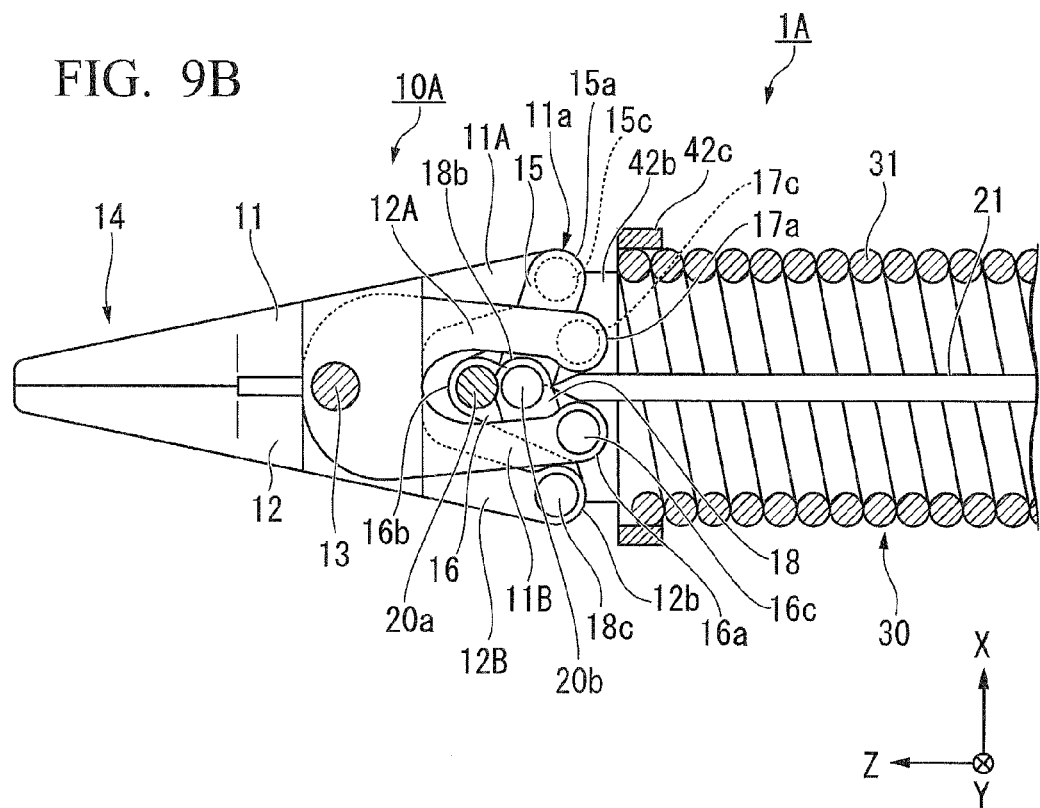
FIG. 9B is a schematic cross-sectional view showing a tip end of a medical treatment tool of a second embodiment of the present invention.
Figure 10:
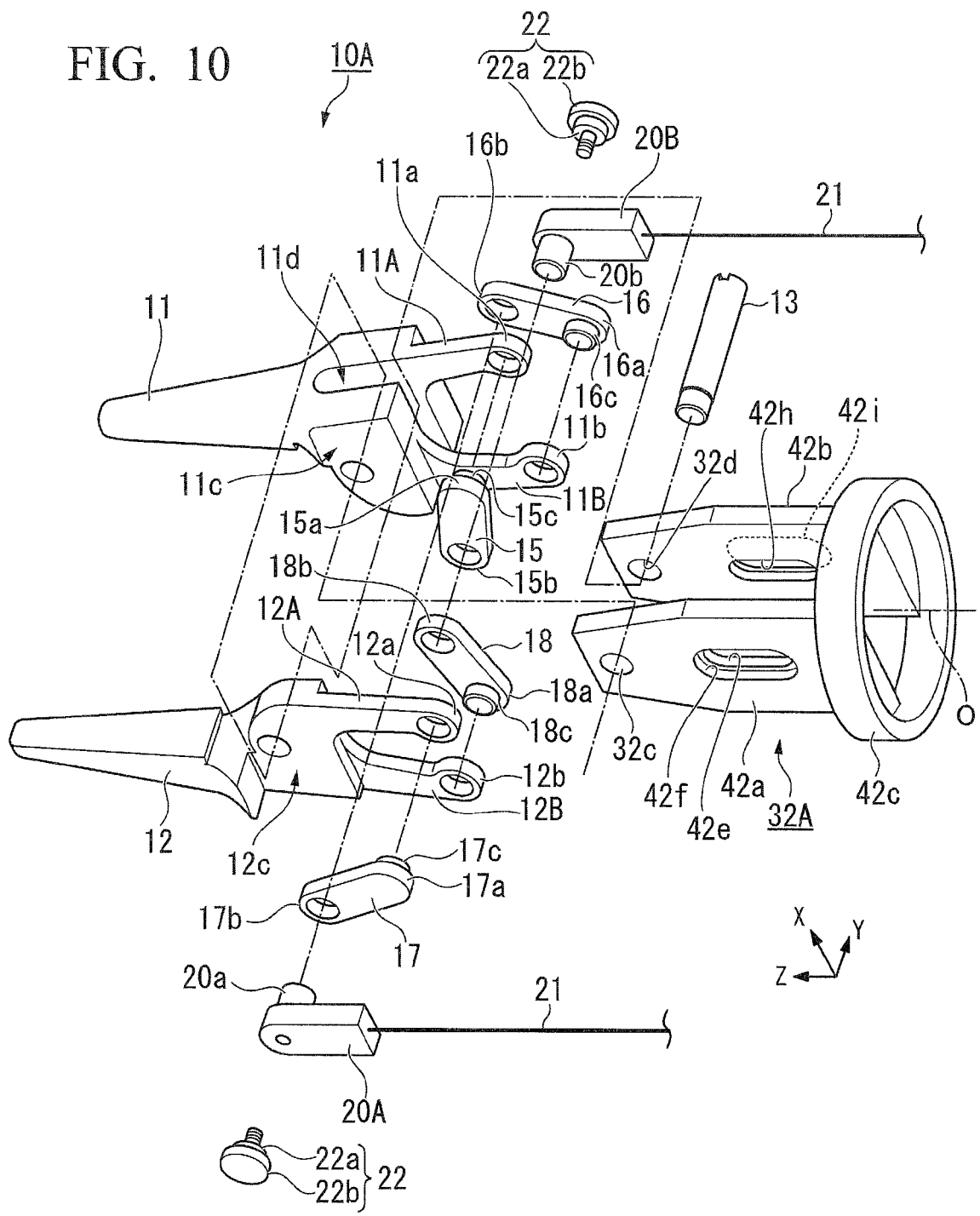
FIG. 10 is a schematic exploded perspective view of the tip end of the medical treatment tool of the second embodiment of the present invention.

FIG. 9A is a schematic front view showing a tip end of a medical treatment tool of a second embodiment of the present invention. FIG. 9B is a schematic cross-sectional view showing the tip end of the medical treatment tool of the second embodiment of the present invention. FIG. 10 is a schematic exploded perspective view of the tip end of the medical treatment tool of the second embodiment of the present invention.

A treatment tool 1A (medical treatment tool) can be mounted on the slave arms 200a to 200d as the above-described treatment tools 240a to 240d.

As shown in FIGS. 9A, 9B, and 10, the schematic configuration of the treatment tool 1A includes a treatment section 10A instead of the treatment section 10 of the first embodiment.

The treatment section 10A has a cover member 32A (substrate) instead of the cover member 32 of the treatment section 10 of the first embodiment, and guide pins 22 are respectively added to the manipulating members 20A and 20B of the first embodiment.

Hereinafter, differences from the first embodiment will mainly be described.

The guide pins 22 have a sliding shaft portion 22a, and a disk-shaped head portion 22b that is coaxial with the sliding shaft portion 22a and has a larger diameter than the sliding shaft portion 22a, and are provided on the back side of the connection rotation shafts 20a and 20b, respectively, in the manipulating members 20A and 20B. The positions of the guide pins 22 are provided at positions where the sliding shaft portions 22a become coaxial with the connection rotation shafts 20a and 20b, respectively.

The guide pins 22 are fixed to the manipulating member 20A, for example by appropriate fixing means, such as screwing, press-fitting, and welding. In the present embodiment, the screwing is adopted as an example, and thereby, the guide pins 22 are detachably fixed to the manipulating members 20A and 20B.

The cover member 32A includes side plate portions 42a and 42b that cover the base ends of the first forceps piece 11 and the second forceps piece 12 from the side, and an annular base end supporting portion 42c that couples the base ends of the side plate portions 42a and 42b and couples the sheath part 30 to the inner peripheral side thereof.

In the present embodiment, the cover member 32A has a shape plane-symmetrical with respect to two planes orthogonal to each other including the central axis O of the base end supporting portion 42c that coincides with the central axis of the end of the sheath part 30 (refer to FIG. 10). The material of the cover member 32A includes, for example, metal or the like.

In the following, similarly to the first embodiment, when referring to relative directions in the treatment section 10A, as shown in FIG. 10, the XYZ coordinate system in which an axis that coincides with the central axis O is the Z-axis, a direction orthogonal to the Z-axis and parallel to the central axis of the forceps rotation shaft 13 is the Y-axis, and an axis orthogonal to the Y-axis and the Z-axis is the X-axis may be used.

The positive direction of the Z-axis is the tip end side in the treatment section 10A, and similarly, the negative direction is on the base end side in the treatment section 10A.

In the present embodiment, symmetry planes in the cover member 32A are a YZ plane and a ZX plane, and the side plate portions 42a and 42b have a shape that is plane-symmetrical with respect to the YZ plane and the ZX plane.

A shaft fixing portion 32c is provided at the end of the side plate portion 42a on the tip end side.

Additionally, an elongate hole 42e (first guide) is provided through the side plate portion 42a in the intermediate portion of the side plate portion 42a closer to the base end side than the shaft fixing portion 32c. The elongate hole 42e allows the sliding shaft portion 22a of the guide pin 22 fixed to the manipulating member 20A to be inserted therethrough without rattling.

The position of the elongate hole 42e is provided at a position where a symmetry plane along the longitudinal direction of the elongate hole 42e becomes the ZY plane. That is, the centerline of the elongate hole 42e in the longitudinal direction passes through the center of the shaft fixing portion 32c, and is located at a position that becomes parallel to the central axis O of the base end supporting portion 42c.

A step hole portion 42f that accommodates the head portion 22b of the guide pin 22 therein is provided on the outer peripheral side of the elongate hole 42e.

For this reason, as shown in FIG. 9A, in an assembled state, the forceps rotation shaft 13 is fixed to the cover member 32A and the first forceps piece 11 and the second forceps piece 12 are rotatably supported with respect to the cover member 32A.

Additionally, the sliding shaft portion 22a and the head portion 22b are arranged so as to be capable of advancing and retracting in the Z-axis direction toward the center of the shaft fixing portion 32c within the elongate hole 42e and the step hole portion 42f, respectively.

Thereby, if the manipulating member 20A is driven along the Z-axis direction by the wire 21, the sliding shaft portion 22a and the manipulating member 20A can be smoothly advanced and retracted in the Z-axis direction with the elongate hole 42e as a guide.

Similarly, as shown in FIG. 10, the side plate portion 42b is provided with a shaft fixing portion 32d, an elongate hole 42h (second guide), and a step hole portion 42i that have positions and shapes that are plane-symmetrical with respect to the YZ plane about the shaft fixing portion 32c, the elongate hole 42e, the step hole portion 42f of the side plate portion 42a, respectively.

For this reason, although not particularly shown, in an assembled state, the sliding shaft portion 22a and the head portion 22b of the guide pin 22 fixed to the manipulating member 20B are arranged so as to be capable of advancing and retracting in the Z-axis direction toward the center of the shaft fixing portion 32d within the elongate hole 42h and the step hole portion 42i, respectively.

Thereby, if the manipulating member 20B is driven along the Z-axis direction by the wire 21, the sliding shaft portion 22a and the manipulating member 20B can be smoothly advanced and retracted in the Z-axis direction with the elongate hole 42h as a guide.

Additionally, the movable ranges of the manipulating members 20A and 20B specified by the elongate holes 42e and 42h are matched with the movable ranges of the manipulating members 20A and 20B in the first embodiment.

Additionally, in the treatment tool 1A, the sheath part 30 is coupled to the cover member 32A via the base end supporting portion 42c of the cover member 32A, and the wire 21 connected to the manipulating members 20A and 20B is inserted into the sheath part 30. Although the wire 21 is not particularly shown, the wire is wound around the wire driving part 33 provided at the other end of the sheath part 30 similarly to the first embodiment.

From such a configuration, the same toggle mechanism as the first embodiment is configured in the treatment section 10A except that the configuration of the first guide and the second guide is different.

That is, in the treatment section 10 of the first embodiment, the movement of the manipulating members 20A and 20B in the Z-axis direction is guided by the guide groove portions 32j and 32k formed inside the cover member 32. In contrast, the treatment section 10 of the present embodiment is different from the first embodiment in that the sliding shaft portions 22a of the guide pins 22 provided coaxially with the connection rotation shafts 20a and 20b of the manipulating members 20A and 20B are guided by the elongate holes 42e and 42h provided in the cover member 32A.

For this reason, the treatment tool 1A of the present embodiment can also perform the same operation as the treatment tool 1 of the first embodiment, and has almost the same action as the treatment tool 1 of the first embodiment.

For example, the reaction force of the output Fo and the reaction force of the output Fo' that act on the connection rotation shafts 20b and 20a, respectively, act in opposite directions. As a result, the reaction forces are cancelled out and become zero. However, in the present embodiment, the connection rotation shafts 20b and 20a inserted through the elongate holes 42e and 42h are not strongly pressed against the inner surfaces of the elongate holes 42e and 42h, respectively, and generation of large friction is suppressed.

[Third Embodiment]

Next, a medical treatment tool of a third embodiment of the present invention will be described.

Figure 11A:
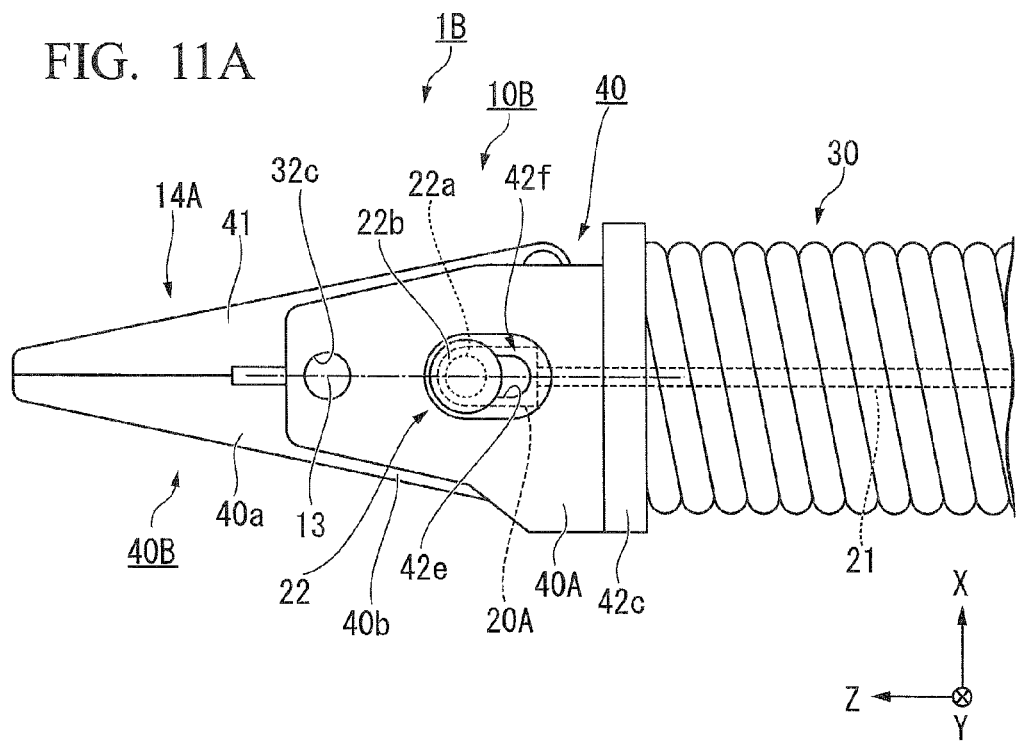
FIG. 11A is a schematic front view showing a medical treatment tool of a third embodiment of the present invention.
Figure 11B:
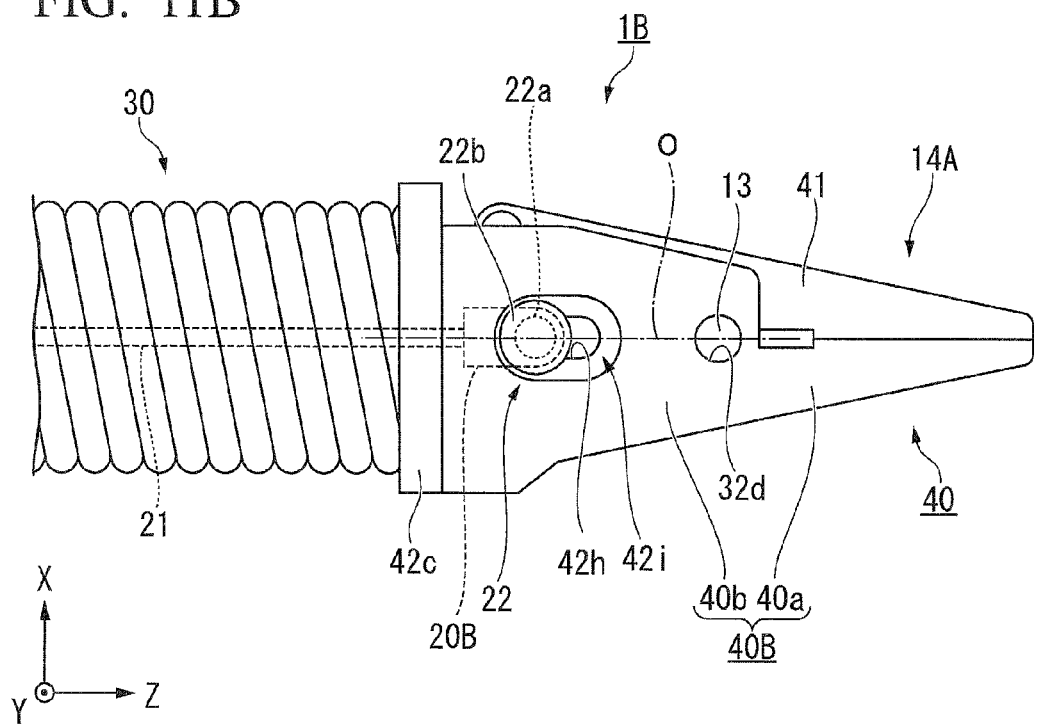
FIG. 11B is a schematic back view showing the medical treatment tool of the third embodiment of the present invention.
Figure 12:
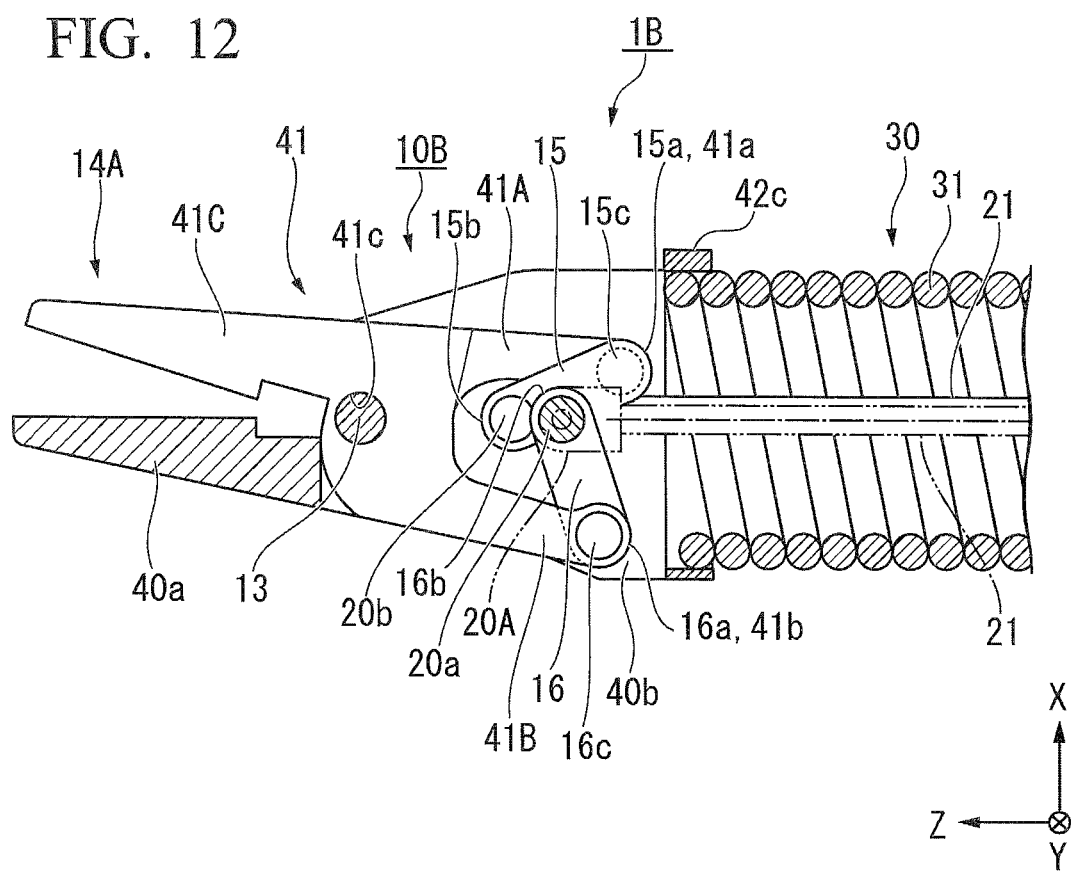
FIG. 12 is a schematic cross-sectional view showing a state where a treatment section of the medical treatment tool of the third embodiment of the present invention is opened.

FIGS. 11A and 11B are a schematic front view and a schematic back view of the medical treatment tool of the third embodiment of the present invention. FIG. 12 is a schematic cross-sectional view showing a state where the treatment section of the medical treatment tool of the third embodiment of the present invention is opened.

A treatment tool 1B (medical treatment tool) of the present embodiment, as shown in FIGS. 11A and 11B, includes a treatment section 10B instead of the treatment section 10A of the treatment tool 1A of the second embodiment, and can be mounted on the slave arms 200a to 200d and used as the treatment tools 240a to 240d of the medical manipulator system shown in FIG. 1 similarly to the second embodiment.

The treatment tool 1B of the present embodiment is different from the treatment tool 1A of the second embodiment in that only one of the pair of treatment tool pieces is rotatable.

Hereinafter, differences from the second embodiment will mainly be described.

In the treatment section 10B of the treatment tool 1B, as shown in FIGS. 11A, 11B, and 12, a forceps piece 41 (treatment tool piece) is fixed to the cover member 40 (substrate) so as to be rotatable by the forceps rotation shaft 13.

The forceps piece 41 includes a shaft hole portion 41c through which the forceps rotation shaft 13 is inserted, at the central portion thereof. A forceps piece portion 41C that presses down an object to be treated is formed closer to the tip end side than the shaft hole portion 41c. Arm portions 41A and 41B extend to the base end side from the shaft hole portion 41c.

The forceps piece portion 41C constitutes a forceps part 14A that is opened and closed to grasp, push open, or press down objects, such as a body tissue or a surgical instrument together with a forceps piece 40a of the cover member 40 to be described below.

The tip end 15a (first end) of the same link member 15 (second link member) as the first embodiment is coupled to an end 41a of the arm portion 41A on the tip end side so as to rotatable with respect to the arm portion 41A via the link rotation shaft 15c provided at the tip end 15a.

Additionally, the tip end 16a (first end) of the same link member 16 (first link member) as the first embodiment is coupled to the end 41b of the arm portion 41B on the tip end side so as to be rotatable with respect to the arm portion 41B via the link rotation shaft 16c provided at the tip end 16a.

However, unlike the first embodiment, other links like the link members 18 and 17 are not connected to the manipulating members 20B and 20A.

The respective central axes of the link rotation shafts 15c and 16c are all parallel to the central axis of the forceps rotation shaft 13.

In this way, the arm portions 41A and 41B and the link members 15 and 16 are links of link mechanisms, respectively, and the link rotation shafts 15c and 16c that are rotary joints of the link mechanisms are provided at the ends 41a and 41b and the tip ends 15a and 16a.

The base ends 15b and 16b (second ends) of the link members 15 and 16 are rotatably connected to the manipulating members 20B and 20A via the connection rotation shafts 20b and 20a, respectively, similarly to the first embodiment.

That is, the central axis of the connection rotation shaft 20b is parallel to the respective central axes of the forceps rotation shaft 13 and the link rotation shaft 15c, and the link member 15 is rotatable relative to the manipulating member 20B. Additionally, the central axis of the connection rotation shaft 20a is parallel to the respective central axes of the forceps rotation shaft 13 and the link rotation shaft 16c, and the link member 16 is rotatable relative to the manipulating member 20A. Additionally, the wire 21 is connected to the manipulating members 20B and 20A, respectively, similarly to the first embodiment.

Additionally, the guide pins 22 are fixed to the manipulating members 20B and 20A so as to become coaxial with the respective connection rotation shafts 20b and 20a, similarly to the first embodiment.

The cover member 40 includes a side plate portion 40A that covers the base end of the forceps piece 41 from the side that is rotatably coupled by the forceps rotation shaft 13, a fixed forceps piece portion 40B provided so as to be fixed to the tip end of the side plate portion 40A, and the same base end supporting portion 42c as the second embodiment that couples the base ends of the side plate portion 40A and the fixed forceps piece portion 40B and that couples the sheath part 30 to the inner peripheral side thereof.

The material of the cover member 40 includes metal or the like similarly to the cover member 32A of the second embodiment.

In the following, substantially similarly to the second embodiment, when referring to relative directions in the treatment section 10B, the XYZ coordinate system in which an axis that coincides with the central axis O is the Z-axis, a direction orthogonal to the Z-axis and parallel to the central axis of the forceps rotation shaft 13 is the Y-axis, and an axis orthogonal to the Y-axis and the Z-axis is the X-axis may be used.

The positive direction of the Z-axis is a direction that goes to the tip end side in the treatment section 10B, and the negative direction of the Z-axis is a direction that goes to the base end side in the treatment section 10B.

As shown in FIG. 11A, the side plate portion 40A is a plate-shaped member of which the outer shape is only slightly different from the side plate portion 42a of the second embodiment, and similarly to the side plate portion 42a, the shaft fixing portion 32c that allows the forceps rotation shaft 13 inserted through the shaft hole portion 41c of the forceps piece 41 to be inserted therethrough, and fixes the position of the forceps rotation shaft is provided at the end of the side plate portion on the tip end side.

Additionally, the elongate hole 42e (first guide) is provided through the side plate portion 40A in the intermediate portion of the side plate portion 40A closer to the base end side than the shaft fixing portion 32c. The elongate hole 42e allows the sliding shaft portion 22a of the guide pin 22 fixed to the manipulating member 20A to be inserted therethrough without rattling.

The elongate hole 42e is located so that the centerline of the elongate hole 42e in the longitudinal direction passes through the center of the shaft fixing portion 32c, and becomes parallel to the central axis O of the base end supporting portion 42c.

The step hole portion 42f that accommodate the head portion 22b of the guide pin 22 therein is provided on the outer peripheral side of the elongate hole 42e.

For this reason, as shown in FIG. 11A, in an assembled state, the forceps rotation shaft 13 is fixed to the cover member 40 and the forceps piece 41 is rotatably supported with respect to the cover member 40.

Additionally, the sliding shaft portion 22a and the head portion 22b connected to the manipulating member 20A are arranged so as to be capable of advancing and retracting in the Z-axis direction toward the center of the shaft fixing portion 32c within the elongate hole 42e and the step hole portion 42f, respectively.

Thereby, if the manipulating member 20A is driven along the Z-axis direction by the wire 21, the sliding shaft portion 22a and the manipulating member 20A can be smoothly advanced and retracted in the Z-axis direction with the elongate hole 42e as a guide.

The fixed forceps piece portion 40B, as shown in FIG. 11B, includes a cover portion 40b connected to the base end supporting portion 42c, and a forceps piece 40a provided on the tip end side of the cover member 40.

The cover portion 40b is a plate-shaped portion that has a shape plane-symmetrical with respect to the side plate portion 40A and the YZ plane, and is provided with the shaft fixing portion 32d, the elongate hole 42h (second guide), and the step hole portion 42i that have positions and shapes that are plane-symmetrical with respect to the YZ plane in correspondence with the shaft fixing portion 32c, the elongate hole 42e, the step hole portion 42f of the side plate portion 40A, respectively.

For this reason, in an assembled state, the sliding shaft portion 22a and the head portion 22b of the guide pin 22 fixed to the manipulating member 20B are arranged so as to be capable of advancing and retracting in the Z-axis direction toward the center of the shaft fixing portion 32d within the elongate hole 42h and the step hole portion 42i, respectively. Thereby, if the manipulating member 20B is driven along the Z-axis direction by the wire 21, the sliding shaft portion 22a and the manipulating member 20B can be smoothly advanced and retracted in the Z-axis direction with the elongate hole 42h as a guide.

The forceps piece 40a is provided so as to abut against the forceps piece portion 41C of the forceps piece 41 rotated about the forceps rotation shaft 13 in close contact therewith at a position aligned with the YZ plane, and constitutes the forceps part 14A together with the forceps piece portion 41C.

For this reason, the pair of treatment tool pieces of the forceps part 14A is constituted by the forceps piece portion 41C rotatably supported with respect to the cover member 40 and the forceps piece 40a that is fixedly supported.

Here, link mechanisms constituted by the arm portions 41A and 41B, the link members 15 and 16, and the manipulating members 20B and 20A will be described. These link mechanisms, as shown in FIGS. 8A and 8B, are arranged in the same positional relationship as the link mechanisms constituted by the arm portions 11A and 11B, the link members 15 and 16, and the manipulating members 20B and 20A related to the first and second embodiments. For this reason, the same toggle mechanism as the first and second embodiments is configured.

Additionally, in the treatment tool 1B, similarly to the treatment tool 1A of the second embodiment, the sheath part 30 is coupled to the base end supporting portion 42c, and the wire 21 connected to the manipulating members 20A and 20B is inserted into the sheath part 30. Although the wire 21 is not particularly shown, the wire is wound around the wire driving part 33 provided at the other end of the sheath part 30 similarly to the first embodiment.

According to such a treatment tool 1B, in a case where the manipulating member 20B is towed by towing the wire 21 using the wire driving part 33 similarly to the second embodiment, the forceps piece portion 41C of the forceps piece 41 is rotated in the closing direction (direction approaching the forceps piece 40a), so that the forceps part 14A can be closed. Additionally, by further towing the wire 21 in the same direction after the forceps part 14A is closed, the grasping force can be increased by a small manipulation force by the action of the toggle mechanism.

Additionally, in a case where the manipulating member 20A is towed by towing the wire 21, the forceps piece portion 41C of the forceps piece 41 is rotated in the opening direction (direction separated from the forceps piece 40a), so that the forceps part 14A can be opened. Additionally, by further towing the wire 21 in the same direction after the forceps part 14A is opened substantially to the maximum, the opening force can be increased by a small manipulation force by the action of the toggle mechanism in a case where an external force that inhibits the forceps part 14A from being opened is received.

Accordingly, similarly to the second embodiment, when the pair of treatment tool pieces is manipulated and opened and closed, the closing force can be increased in a case where the treatment tool pieces are closed and the opening force can be increased even in a case where the treatment tool pieces are opened.

[Fourth Embodiment]

Next, a fourth embodiment of the present invention will be described.

Figure 13A:
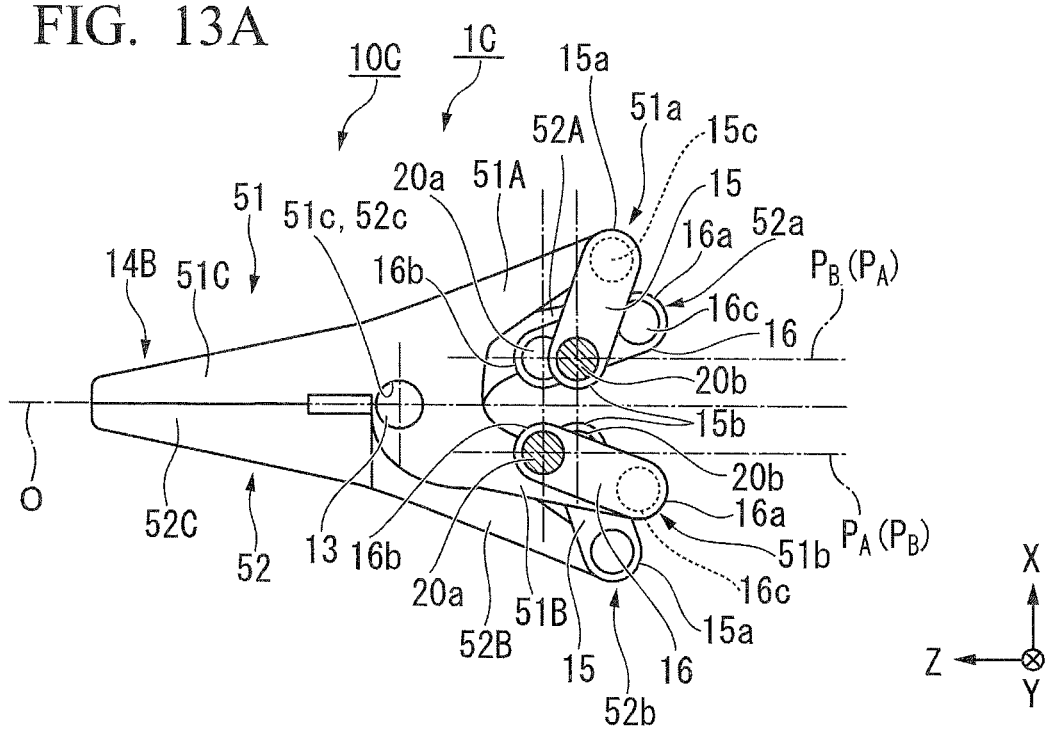
FIG. 13A is a schematic cross-sectional view showing a state where a treatment section of a medical treatment tool of a fourth embodiment of the present invention is closed.
Figure 13B:
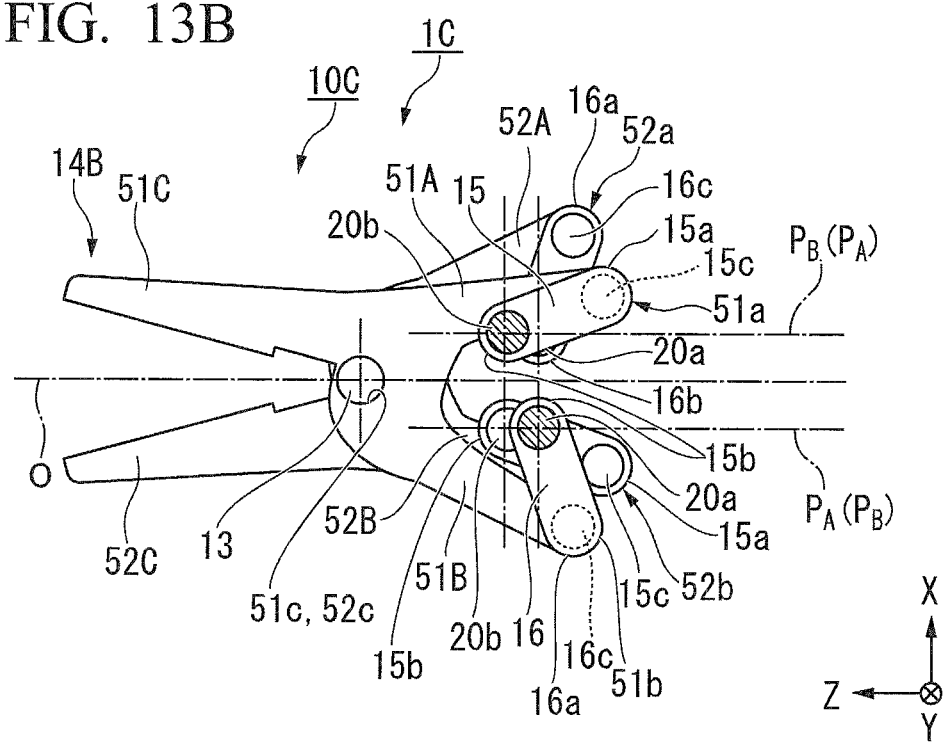
FIG. 13B is a schematic cross-sectional view showing a state where the treatment section of the medical treatment tool of the fourth embodiment of the present invention is opened.
Figure 14:
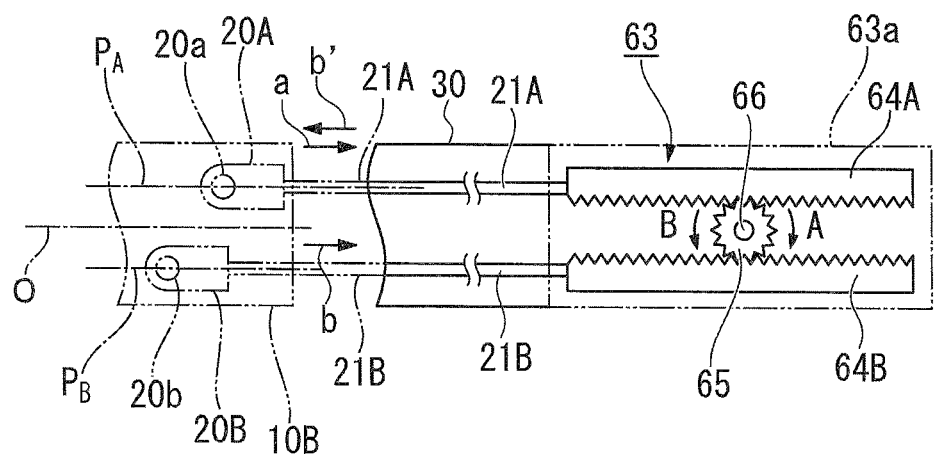
FIG. 14 is a schematic front view showing an example of a rack-and-pinion driving part used for opening and closing of the treatment section of the medical treatment tool of the fourth embodiment of the present invention.

FIG. 13A shows a state where a treatment section of a medical treatment tool of the fourth embodiment of the present invention is closed. FIG. 13B is a schematic cross-sectional view showing a state where the treatment section of the medical treatment tool of the fourth embodiment of the present invention is opened. FIG. 14 is a schematic front view showing an example of a rack-and-pinion driving part used for opening and closing of the treatment section of the medical treatment tool of the fourth embodiment of the present invention.

A treatment tool 1C (medical treatment tool) of the present embodiment, as shown in FIGS. 13A and 13B, includes the treatment section 10C instead of the treatment section 10A of the treatment tool 1A of the second embodiment. Additionally, as shown in FIG. 14, the treatment tool includes a rack-and-pinion driving part 63 and wires 21A and 21B instead of the wire driving part 33 and the wire 21 of the second embodiment. However, in conformity with the configuration of the treatment section 10B, two sets of rack-and-pinion driving parts 63 are provided and two pairs of wires 21A and 21B are provided.

The treatment tool 1C of such a configuration, similarly to the second embodiment, can be mounted on the slave arms 200a to 200d and used as the treatment tools 240a to 240d of the medical manipulator system shown in FIG. 1.

In the treatment tool 1A of the second embodiment, both of the pair of treatment tool pieces are rotatably supported by the substrate and the link mechanisms that manipulate the rotation operations using one pair of manipulating members 20A and 20B are provided. In contrast, the treatment tool 1C of the present embodiment is different from the second embodiment in that the rotation operations of the respective treatment tool pieces are independently manipulated, respectively, similarly to a case where one pair of treatment tool pieces is rotatably supported, respectively. For this reason, a configuration is provided in which the toggle mechanism that rotates one treatment tool piece (first treatment tool piece) in the third embodiment is also provided at the other treatment tool piece (second treatment tool piece). For this reason, if one treatment tool piece and its toggle mechanism are described, the configuration of the other side can be easily understood.

Hereinafter, differences from the second embodiment will mainly be described. Additionally, since the descriptions regarding the two sets of configurations are almost duplicated, description will be simplified by writing corresponding members in parentheses.

The treatment section 10C of the treatment tool 1C, as shown in FIGS. 13A and 13B, a first forceps piece 51 and a second forceps piece 52 (a pair of treatment tool pieces) are fixed to a substrate (not shown) so as to be rotatable by the forceps rotation shaft 13.

The first forceps piece 51 (second forceps piece 52) includes a shaft hole portion 51c (52c) through which the forceps rotation shaft 13 is inserted, at the central portion thereof A forceps piece portion 51C (52C) that presses down an object to be treated is formed closer to the tip end side than the shaft hole portion 51c (52c). Arm portions 51A and 51B (52A and 52B) extend to the base end side from the shaft hole portion 51c (52c).

The forceps piece portions 51C and 52C constitute a forceps part 14B that is opened and closed to grasp, push open, or press down objects, such as a body tissue or a surgical instrument.

The tip end 15a (first end) of the same link member 15 (second link member) as the first embodiment is coupled to an end 51a (52b) of the arm portion 51A (52B) on the base end side so as to rotatable with respect to the arm portion 51A (52B) via the link rotation shaft 15c provided at the tip end 15a.

Additionally, the tip end 16a (first end) of the same link member 16 (first link member) as the first embodiment is coupled to the end 51b (52a) of the arm portion 51B (52A) on the base end side so as to be rotatable with respect to the arm portion 51B (52A) via the link rotation shaft 16c provided at the tip end 16a.

However, unlike the second embodiment, other links like the link members 18 and 17 are not connected to the manipulating members 20B and 20A.

The respective central axes of the respective link rotation shafts 15c and 16c are all parallel to the central axis of the forceps rotation shaft 13.

In this way, the arm portions 51A and 51B (52B and 52A) and the link members 15 and 16 are links of link mechanisms, respectively. The ends 51a and 51b (52b and 52a) and the tip ends 15a and 16a are provided with the link rotation shafts 15c and 16c that are rotary joints of the link mechanisms.

The base ends 15b and 16b (second ends) of the link members 15 and 16 are rotatably connected to the manipulating members 20B and 20A via the connection rotation shafts 20b and 20a of the manipulating members 20B and 20A, respectively, similarly to the second embodiment. Illustration of the manipulating members 20B and 20A and the wires 21A and 21B is omitted in FIGS. 13A and 13B because of difficulties in visibility due to overlapping.

That is, the central axis of each connection rotation shaft 20b is parallel to the respective central axes of the forceps rotation shaft 13 and the link rotation shaft 15c, and each link member 15 is rotatable relative to each manipulating member 20B. Additionally, the central axis of each connection rotation shaft 20a is parallel to the respective central axes of the forceps rotation shaft 13 and each link rotation shaft 16c, and each link member 16 is rotatable relative to each manipulating member 20A.

In the present embodiment, as shown in FIG. 14, the wires 21B and 21A are connected to the respective manipulating members 20B and 20A, respectively. In the respective manipulating members 20B and 20A, similarly to the second embodiment, the guide pins 22 (not shown) are fixed to the respective connection rotation shafts 20b and 20a, and are provided so as to be movable within guides, such as elongate holes provided in the substrate (not shown).

However, unlike the second embodiment, the advance and retraction axis $P_B$ ($P_A$) of the base end 15b (16b) of the link member 15 (16) is set to an axis shifted in parallel to the tip end 15a (16a) side (X-axis positive (negative) direction side) from the central axis O.

In link mechanisms including such arm portions 51A and 51B (52B, 52A) and link members 15 and 16, the positional relationship among the forceps rotation shaft 13, the tip ends 15a and 16a, and the connection rotation shafts 20b and 20a is the same as the positional relationship between the rotary joint of the link mechanisms that constitute the toggle mechanism of the first embodiment except that the advance and retraction axes $P_B$ and $P_A$ are shifted in parallel from the central axis O.

Next, the rack-and-pinion driving part 63 will be described.

The two sets of rack-and-pinion driving parts 63 are detachably connected to an adapter in which a rotating mechanism is provided as a driving mechanism, among the adapters 220a to 220d of FIG. 1. Additionally the rack-and-pinion driving part 63 is a member that transmits the power supplied from a slave arm corresponding to the connected adapter to the wire 21A (first wire) and the wire 21B (second wire).

In the following, a case where the two sets of rack-and-pinion driving parts 63 are mounted on an adapter 220b and receive the power from the slave arm 200b will be described as an example.

As for the schematic configuration of each rack-and-pinion driving part 63, as shown in FIG. 14, in the present embodiment, a drive shaft 66, a pinion 65, a rack 64A (first rack), and a rack 64B (second rack) are provided inside a housing 63a that has such a shape that the housing is attachable to and detachable from the adapter 220b. Since the configurations of the respective rack-and-pinion driving parts 63 are the same, FIG. 14 shows only one rack-and-pinion driving part 63.

When the drive shaft 66 is rotatably held by the housing 63a and the housing 63a is mounted on the adapter 220b, an end (not shown) is configured to be capable of being coupled to a power transmission shaft (not shown) of the adapter 220b. The end (shown in FIG. 11) of the drive shaft 66 is fixed to the pinion 65.

The pinion 65 is fixed to the end of the drive shaft 66, is rotated with the rotation of the drive shaft 66, and is engaged with the racks 64A and 64B that face each other and are arranged in parallel.

The rack 64A (64B) has the other end of the wire 21A (21B) of which one end is connected to the manipulating member 20A (20B) fixed thereto, and is supported by the housing 63a so as to be able to move linearly in a constant direction with the rotation of the pinion 65.

For this reason, in the present embodiment, for example, if the pinion 65 is rotated in the direction (shown counterclockwise direction) of arrow B of FIG. 14, the rack 64B moves the wire 21B in a direction in which the wire is towed to the rack-and-pinion driving part 63 side, and the rack 64A moves the wire 21A in a direction in which the wire is pushed out to the treatment section 10B side. On the contrary, if the pinion 65 is rotated in the direction of A as shown, operation opposite to this is performed.

According to such a treatment tool 1C, the forceps part 14B can be opened and closed by towing either of the wires 21A and 21B by the rack-and-pinion driving part 63.

In the following, for the sake of simplicity, a case where the first forceps piece 51 and the second forceps piece 52 perform symmetrical operation by driving each rack-andpinion driving part 63 similarly will be described as an example. However, in the present embodiment, the first forceps piece 51 and the second forceps piece 52 are respectively provided with two sets of rack-and-pinion driving parts 63 that rotate independently. For this reason, it is possible for the position of any of the first forceps piece 51 and the second forceps piece 52 to be fixed, or to change the opening and closing amount or opening and closing speed of the first and second forceps pieces mutually.

In order to open the forceps part 14B from a state where the forceps part 14B shown in FIG. 13A is closed, each pinion 65 of each rack-and-pinion driving part 63 is rotated in the direction of arrow A of FIG. 14. Thereby, each wire 21A is towed to the rack-and-pinion driving part 63 side, and each manipulating member 20A to which each wire 21A is connected is towed in a direction separated from the forceps rotation shaft 13 on the advance and retraction axis $P_A$.

Thereby, each connection rotation shaft 20*a* moves, an angle formed by each link member 16 with respect to the advance and retraction axis $P_A$ increases and approaches 90°, and the arm portions 51B and 52A coupled to the link rotation shaft 16*c* of the tip end 16*a* of each link member 16 are rotated.

At this time, the arm portion 51B is rotated in the shown clockwise direction, and the arm portion 52A is rotated by the shown counterclockwise direction. Thereby, the forceps piece portions 51C and 52C are rotated in the directions leading to separation from each other, and the forceps part 14B is opened.

In this opening operation, in the link including the arm portions 51A and 52B, the ends 51*a* and 52*b* of the arm portions 51A and 52B rotate, respectively, in directions in which the link rotation shaft 15*c* of the link member 15 is brought close to the advance and retraction axis $P_B$. Therefore, the connection rotation shaft 20*b* moves in a direction approaching the forceps rotation shaft 13 in cooperation with the wire 21B connected to the rack 64A being pushed out in the direction approaching the forceps rotation shaft 13 on the advance and retraction axis $P_B$.

If the reverse operation of the above operation is performed, the opened forceps part 14B can be closed.

Additionally, by further towing the wire 21B in the same direction after the forceps part 14B is closed, the grasping force can be increased by a small manipulation force by the action of the toggle mechanism.

Additionally, in a case where the manipulating member 20A is towed by towing the wire 21A, the wire 21A is further towed in the same direction after the forceps part 14B is opened substantially to the maximum. Therefore, the opening force can be increased by a small manipulation force by the action of the toggle mechanism in a case where an external force that inhibits the forceps part 14B from being opened is received.

Accordingly, similarly to the second embodiment, when the pair of treatment tool pieces is manipulated and opened and closed, the closing force can be increased in a case where the treatment tool pieces are closed and the opening force can be increased even in a case where the treatment tool pieces are opened.

Although the respective embodiments of the present invention have been described above, the technical scope of the present invention is not limited to the above respective embodiments, and without departing from the scope of the present invention, various changes or omissions can be made to respective constituent elements or constituents of the respective embodiments can be combined together.

For example, in the above third and fourth embodiments, it is possible to change the configuration in which the guides are the elongate holes to the configuration in which the guides are the guide groove portions in the above first embodiment.

Additionally, it is possible to change the configuration in which the wire is towed using the wire driving part 33 of the above first to third embodiments to the configuration in which the wires are towed using the rack-and-pinion driving parts 63 of the above fourth embodiment.

Although an example where the wire is used as a member that tows the manipulating members has been described in the description of the respective embodiments, a configuration in which a rod is used instead of the wire may be adopted.

In this case, it is not necessary to provide the guides, such as the elongate holes 42*e* and 42*h* if the manipulating members can be advanced and retracted along the axis of the rod itself by giving appropriate rigidity to the rod.

Additionally, although an example in which the tension application portions 36A and 36B are provided at the wire driving part 33 has been described in the description of the above first to third embodiments, a configuration in which at least any of the tension application portions 36A and 36B is eliminated depending on the rigidity of the wire 21 may be adopted.

Additionally, although an example where the guide pins 22 are fixed to the manipulating members 20A and 20B and the sliding shaft portions 22*a* of the guide pins 22 are inserted into the elongate holes has been described in the description of the above second to fourth embodiments, a configuration where the connection rotation shafts 20*a* and 20*b* are inserted into guides, such as elongate holes may be adopted.

Additionally, an example in which the treatment tool is provided at a manipulator in a medical manipulator system has been described in the description of the above respective embodiments. However, the treatment tool of the present invention is not limited to an aspect in which the treatment tool is connected to the manipulator, and can also be used as a treatment tool that is not connected to the manipulator.

For example, the treatment tool 1 of the first embodiment can be used as an independent treatment tool as an operator performs manual manipulation to rotate the drive shaft 35 of the wire driving part 33.

While preferred embodiments of the present invention have been described, the present invention is not limited to the embodiments.

Additions, omissions, substitutions, and other variations may be made to the present invention without departing from the spirit and scope of the present invention. The present invention is not limited by the above description, but by the appended claims.

The invention claimed is:

1. A medical treatment tool comprising:
a pair of treatment tool pieces comprising a first treatment tool piece and a second treatment tool piece,
wherein the first treatment tool piece extends along a longitudinal axis and comprises:
a treatment surface provided closer to a distal end of the first treatment tool piece along the longitudinal axis;
an intermediate portion that defines a hole that allows a rotation shaft to pass therethrough, wherein the first treatment tool piece is rotatably supported by the rotation shaft with respect to a substrate to rotate the treatment surface towards and away from the second treatment tool piece to open and close the pair of treatment tool pieces; and
a pair of arm portions provided closer to a proximal end along the longitudinal axis than the rotation shaft in the first treatment piece;
a first manipulating member configured to be movable parallel to an advance and retraction axis with respect to the substrate wherein the first manipulating member is configured to be towed parallel to the advance and retraction axis and away from the pair of treatment tool pieces to rotate the pair of treatment tool pieces in a direction in which the pair of treatment tool pieces is opened;
a second manipulating member configured to be movable parallel to the advance and retraction axis with respect to the substrate wherein the second manipulating member is configured to be towed parallel to the advance and retraction axis and away from the pair of treatment tool pieces to rotate the pair of treatment tool pieces in a direction in which the pair of treatment tool pieces is closed;
a first link member which has a first end coupled to a first arm portion of the pair of arm portions of the first treatment tool piece and a second end coupled to the first manipulating member; and
a second link member which has a first end coupled to a second arm portion of the pair of arm portions of the first treatment tool piece and a second end coupled to the second manipulating member,
wherein a first rotation axis center where the second end of the first link member is coupled to the first manipulating member and a second rotation axis center where the second end of the second link member is coupled to the second manipulating member are positioned closer to the distal end of the first treatment tool piece than a third rotation axis center where the first end of the first link member is coupled to the first arm portion of the pair of arm portions of the first treatment tool piece and a fourth rotation axis center where the first end of the second link member is coupled to the second arm portion of the pair of arm portions of the first treatment tool piece,
wherein as the second end of the first link member is made to advance and retract along the advance and retraction axis through movement of the first manipulating member, a distance between the third rotation axis center and the advance and retraction axis is shorter than a length of a distance between a fifth rotation axis center where the first treatment tool piece rotates about the rotation shaft and the third rotation axis center,
wherein a length prescribed by projecting a line segment connecting the first rotation axis center and the fifth rotation axis center on the advance and retraction axis is shorter than a length prescribed by projecting a line segment connecting the third rotation axis center and the fifth rotation axis center,
wherein as the second end of the second link member is made to advance and retract along the advance and retraction axis through movement of the second manipulating member, a distance between the fourth rotation axis center and the advance and retraction axis is shorter than a length of a distance between the fifth rotation axis center and the fourth rotation axis center, and
wherein a length prescribed by projecting a line segment connecting the second rotation axis center and the fifth rotation axis center on the advance and retraction axis is shorter than a length prescribed by projecting a line segment connecting the fourth rotation axis center and the fifth rotation axis center.

2. The medical treatment tool according to claim 1, wherein the first treatment tool piece and the second treatment tool piece are rotatably supported with respect to the substrate,
wherein the first treatment tool piece is coupled with the first manipulating member via the first link member, and
wherein the second treatment tool piece is coupled with the second manipulating member via the second link member.

3. The medical treatment tool according to claim 2, wherein the first link member coupled to the first treatment tool piece and the first link member coupled to the second treatment tool piece are coupled to the first manipulating member via one first connection rotation shaft at the respective second ends thereof, and
wherein the second link member coupled to the first treatment tool piece and the second link member coupled to the second treatment tool piece are coupled to the second manipulating member via one second connection rotation shaft at the respective second ends thereof.

4. The medical treatment tool according to claim 2, wherein the substrate comprises a first guide that extends parallel to the advance and retraction axis and a second guide that extends parallel to the advance and retraction axis,
wherein the first manipulating member is supported so as to be movable along the first guide, and
wherein the second manipulating member is supported so as to be movable along the second guide.

5. The medical treatment tool according to claim 1, further comprising:
a wire which has a first end coupled to the first manipulating member and a second end coupled to the second manipulating member; and
a wire driving part in which the wire is wound,
wherein the wire driving part is configured to move the first manipulating member to advance and retract parallel to the advance and retraction axis and to move the second manipulating member to advance and retract parallel to the advance and retraction axis.

6. The medical treatment tool according to claim 1, further comprising:
a rack-and-pinion driving part comprising a first rack, a second rack, and a pinion engaged with the first rack and the second rack, and that drives to advance and retract the first rack and the second rack in mutually opposite directions by a rotation of the pinion;
a first wire that couples the first rack and the first manipulating member; and
a second wire that couples the second rack and the second manipulating member,
wherein the first and second wires are configured to be driven to advance and retract by the rack-and-pinion driving part to move the first manipulating member parallel to the advance and retraction axis and move the second manipulating member parallel to the advance and retraction axis.

7. The medical treatment tool according to claim 5, further comprising:
   a tension application portion configured to apply tension to the wire, wherein the tension application portion is provided in a middle of the wire.

8. A manipulator comprising:
   the medical treatment tool according to claim 1.

\* \* \* \* \*